(12) United States Patent
Van Eijk et al.

(10) Patent No.: US 7,217,516 B2
(45) Date of Patent: May 15, 2007

(54) METHODS AND KITS COMPRISING AFLP PRIMERS, AND RAMP PRIMERS WITH A PART COMPLEMENTARY TO A COMPOUND MICROSATELLITE REPEAT AND AN ANCHOR PART COMPLEMENTARY TO NUCLEOTIDES ADJACENT TO THE REPEAT

(75) Inventors: Michael Josephus Theresia Van Eijk, Herpen (NL); Johan Dominicus Peleman, Wageningen (NL); Maria Johanna De Ruiter-Bleeker, Renkum (NL)

(73) Assignee: Keygene N.V., Wageningen (NL)

( * ) Notice: Subject to any disclaimer, the term of this patent is extended or adjusted under 35 U.S.C. 154(b) by 476 days.

(21) Appl. No.: 10/276,401

(22) PCT Filed: May 15, 2001

(86) PCT No.: PCT/NL01/00367

§ 371 (c)(1),
(2), (4) Date: Apr. 28, 2003

(87) PCT Pub. No.: WO01/88189

PCT Pub. Date: Nov. 22, 2001

(65) Prior Publication Data

US 2003/0190645 A1 Oct. 9, 2003

(30) Foreign Application Priority Data

May 15, 2000 (EP) .................. 00201725
Jan. 12, 2001 (EP) .................. 01200104

(51) Int. Cl.
*C12Q 1/68* (2006.01)
*C12P 19/34* (2006.01)

(52) U.S. Cl. .................... 435/6; 435/91.2

(58) Field of Classification Search ........... 435/6, 435/91.2
See application file for complete search history.

(56) References Cited

U.S. PATENT DOCUMENTS 5,874,215 A * 2/1999 Kuiper et al. ............. 435/6
5,955,276 A 9/1999 Morgante et al.

FOREIGN PATENT DOCUMENTS

| EP | 0 534 858 | * | 3/1993 |
| EP | 0 721 987 | | 7/1996 |
| WO | WO 98/42867 | | 10/1998 |
| WO | WO 00/24935 | | 5/2000 |

OTHER PUBLICATIONS

Wu et al. "Detection Of Microsatellite Polymorphisms Without Cloning" *Nucleic Acids Research* 22(15) :3257-3258 (1994).
Witsenboer et al. "Identification, Genetic Localization, And Allelic Diversity Of Selectively Amplified Microsatellite Polymorphic Loci In Lettuce And Wild Relatives (*Lactuca* Spp.)" *Genome* 40 (1997).
Vos et al. "AFLP: A New Technique for DNA Fingerprinting" *Nucleic Acids Research* 23(21) :4407-4414 (1995).
Sanchez De La Hoz et al. "Simple Sequence Repeat Primers Used in Polymerase Chain Reaction Amplifications to Study Genetic Diversity in Barley" *Genome* 39: 112-117 (1996).

* cited by examiner

*Primary Examiner*—Kenneth R. Horlick
(74) *Attorney, Agent, or Firm*—Browdy and Neimark, PLLC

(57) ABSTRACT

The present invention discloses methods for identifying and analysing microsatellite-associated polymorphisms between different DNA samples. Different DNA samples, e.g. from different individuals, are analysed using a PCR based on the combination of a RAMP-primer and an AFLP-primer and polymorphisms between the different DNA samples are identified. The polymorphisms thus identified may be isolated and further analysed by e.g. DNA sequence analysis both upstream and downstream from the microsatellite-associated polymorphism. These sequences may subsequently be used to devise and synthesise new means for analysis of the polymorphic locus, such as e.g. PCR-primer pairs or oligonucleotide probes.

17 Claims, 10 Drawing Sheets

Fig 2
1     Sequencing RAMP-fragment
2     Amplification using internal PCR-primer-1 and Mse I-primer
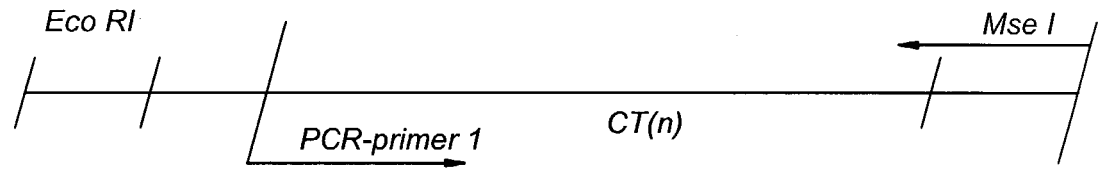
3     Sequencing amplified product PCR-primer-1 and Mse I-primer
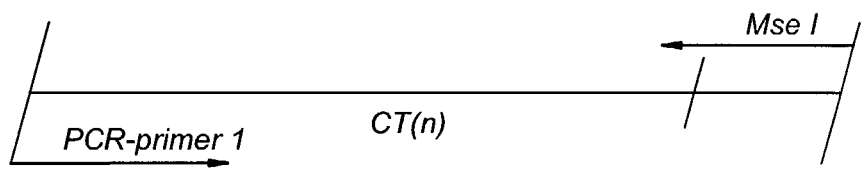
4     Amplification using PCR-primers 1 and 2
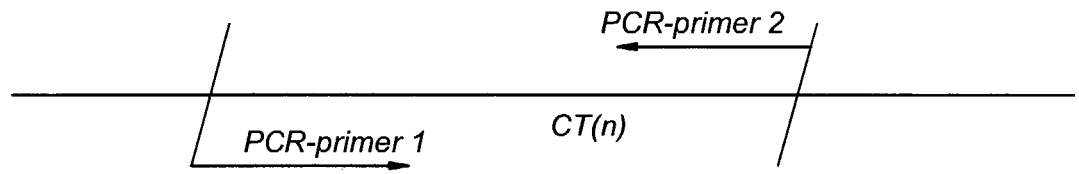

TYPE CA

TYPE CA

Fig 8a

A. Nucleotide sequences of lettuce fragments (the numbers refer to the SEQ IDs)

```
11. TCGACACAAAATCCGAGGCTGTCAGGCCCCCCACGACGTGGTGAAGAAGCCACGACGTGGTATTGTGATTGATGGGT
12. ------------------------------------------------------------------------------
13. ------------------------------------------------------------------------------

11. GCCAGGTGCGTCACGAAACGTCTCGTCAACAGAAGAGGANTAGAATCCCTCACCACGACGTGGTGACATGGCGCCCA
12. ------------------------------------------------------------------------------
13. ------------------------------------------------------------------------------

11. AATTAGGGCTATAAATAGCAGCCGAAGGTGTTGGGTTCCATTGCTTATTTCTTCTCTCTCTCTCTCTCTCTCT
12. ---------------------------------------------------XXXX---------------------
13. ---------------------------------------------------XXXXXX-------------------

11. CTCTCTCTCTCTCTCTCTCTCGTGCCGTC  (260 bp)
12. -----------------------------  (256 bp)
13. -----------------------------  (254 bp)
```

Fig 8b

B. Nucleotide sequences of pickle fragments (the numbers refer to the SEQ IDs)

```
22. GAATTCCGGGGCGARAACCAGAAGAAATAGAGAGGTATTGGATAATGACTCACCTTGAAGGGTTTGGAAAAAGAAGA
23. ------------------------------------------------------------------------------

22. AGAGGATGAGAGAGACAGAGAGATACAGGCAATGAGGGTTCAGKCAATAAGTCCTCAAAGACTTCTGATGGGTTCTC
23. ------------------------------------------------------------------------------

22. TACTTCATCGTTTGTGGTCTCCCTGAAGATAACAATCTCCCTAATAGCTTTAGTGTATTACAAGTACCCTTTCTAAG
23. ---------------------XXXXXXXXXX-----------------------------------------------

22. AACACATGGTATGGAACAGAGCTATCTTTTATCAATCAAATAACACAGTATAATTTATGATTCCAAATCAAAAACTA
23. ------------------------------------------------------------------------------

22. AAGCAAAGAGCAAAGACTATTCAGTTCTTTTGTGTGTGTGTGTGTGTGTGTGTGTAAATCGAG  (373 bp)
23. ----------------------------XXXXXX----------------------------  (357 bp)
```

Fig 8c

C. Nucleotide sequences of maize fragments (the numbers refer to the SEQ IDs)

```
30 CTGCAGCCCTGCCGACCAGTCTCCGTTCCCCTTCTTGTATTTCATGGTGAGTAATAAGATTCTCTCTCTCTCTCT
31.---------A-------------------------------------------A---------------------T-TG

30.TGTTTTTTCTGTCGAAAAATGGGAATCGCTACAAGTAGCATCCGTATTTTCCATTTTTTCCCGATACGATTCTCTCT
31.GT--------A---------------T-------------------------------------------XX-----

30.TCTCTCTCCGCTTATC (170 bp)
31.---------------- (168 bp)
```

Fig 8d

D. Nucleotide sequences of pepper fragments (the numbers refer to the SEQ IDs)

```
34.GAATTCCATAAGGAGAGCTCGAATNAATGATCCATTTTAGTTGAAAGTTGAAATACAGTGCATCCTCTAATAGGAG
35.------------------------------------------------A------------------------GG

34.TGTGTGTGTGTGTGCGCTTATC (98 bp)
35.GXXX------------------ (95 bp)
```

A                    B                    C

METHODS AND KITS COMPRISING AFLP PRIMERS, AND RAMP PRIMERS WITH A PART COMPLEMENTARY TO A COMPOUND MICROSATELLITE REPEAT AND AN ANCHOR PART COMPLEMENTARY TO NUCLEOTIDES ADJACENT TO THE REPEAT

FIELD OF THE INVENTION

The present invention relates to a method for identifying and analysing nucleic acid sequences that contain or are associated with highly repetitive nucleotide sequences known as microsatellites. In particular, the invention provides a method for identifying and analysing nucleic acid sequences based upon polymorphisms associated with such microsatellites.

BACKGROUND OF THE INVENTION

Various methods for analysing nucleic acid sequences are known in the art. Often, such techniques involve amplification—such as by PCR—of one or more parts of the nucleic acid(s) of a mixture of restriction fragments generated from the nucleic acid(s). The amplified mixture thus obtained is then analysed, e.g. by detection of one or more of the amplified fragments. For example, the amplified fragments may be separated on the basis of differences in length or molecular weight, such as by gel-electrophoresis, after which the amplified fragments are visualised, e.g. by autoradiography of the labelled amplified fragments or blotting followed by hybridisation. The resulting pattern of bands is referred to as a "(DNA) fingerprint".

Usually in DNA fingerprinting, fingerprints of closely related species, subspecies, varieties, cultivars, races or individuals are compared. Such related fingerprints can be identical or very similar, i.e. contain a large number of corresponding—and therefore less informative—bands. Differences between two related DNA-fingerprints are referred to as "DNA-polymorphisms". These are amplified fragments—i.e. bands—, which are unique in or for a fingerprint and/or for a subset of fingerprints. The presence or absence of such polymorphic fragments in a fingerprint—or the pattern thereof—can be used as a genetic marker, for instance to identify a specific species, subspecies, variety, cultivar, race or individual; to establish the presence or absence of a specific inheritable trait and/or of a specific gene; and/or to determine the state of a disease. For a further discussion of DNA-fingerprinting, DNA-polymorphisms, genotyping, PCR and similar amplification techniques, as well as the techniques and materials used therein, reference is inter alia made to the prior art mentioned hereinbelow, as well as to the standard handbooks.

One DNA-fingerprinting technique—which is advantageous in that it requires no prior knowledge of the sequence to be analysed—is selective restriction fragment amplification or AFLP®. In general, AFLP® comprises the steps of:
(a) digesting a nucleic acid, in particular a DNA, with one or more specific restriction endonucleases, to fragment the DNA into a corresponding series of restriction fragments;
(b) ligating the restriction fragments thus obtained with a double-stranded synthetic oligonucleotide adapter, one end of which is compatible with one or both of the ends of the restriction fragments, to thereby produce tagged restriction fragments of the starting DNA;
(c) contacting the tagged restriction fragments under hybridising conditions with a oligonucleotide primer;
(d) amplifying the tagged restriction fragment hybridised with the primers by PCR or a similar technique so as to cause further elongation of the hybridised primers along the restriction fragments of the starting DNA to which the primers hybridised; and
(e) detecting, identifying or recovering the amplified or elongated DNA fragment thus obtained.

The AFLP-fingerprint thus obtained provides information on sequence variation m (subsets of) the restriction enzyme sites used for preparation of the AFLP template and the nucleotide(s) immediately adjacent to these restriction enzyme sites in the starting DNA. By comparing AFLP-fingerprints from related individuals, again polymorphic fragments (also referred to as "AFLP-markers") can be detected/identified, e.g. for the purposes mentioned hereinabove.

For a further description of AFLP® its advantages, its embodiments, as well as the techniques, enzymes, adapters, primers and further compounds and tools used therein, reference is made to EP-A-0 534 858 and co-pending European applications 98.202.5496 and 98.202.4515, all by applicant.

However, although AFLP® is a very efficient technique for identifying and analysing polymorphisms in random subsets of nucleic acid sequences, it cannot be used to analyse nucleic acid sequences for polymorphisms/markers associated with particular sequences such as highly polymorphic microsatellites.

It is known that the genome of many—if not all—eukaryotic organisms contains a large number of repeating nucleotide sequences, which are variously referred to as "simple sequence repeats" or "SSRs"; "simple sequence length polymorphisms" or "SSLPs"; "dinucleotide, trinucleotide, tetranucleotide or pentanucleotide repeats";"(short) tandem repeats" or "STRs"; and/or "microsatellites" (the term mainly used in the present description). It is also known that such microsatellites may provide codominant genetic markers with a high degree of allelic polymorphism. Consequently, microsatellites generally have a higher Polymorphism Information Content (PIC) than bi-allelic markers, such as most AFLP markers. Accordingly, various techniques have been developed in the art to analyse nucleic acid sequences for the presence or absence of such microsatellite-associated polymorphisms that may be used as genetic markers.

Usually, these known techniques involve the amplification of the nucleic acid or a mixture of restriction fragments generated from the nucleic acid with a combination of (at least) two primers, which either both flank the repeat motif of a microsatellite present in the starting nucleic acid, or of which at least one is (intended to be) complementary to a microsatellite sequence present in the starting nucleic acid (also referred to as the "microsatellite-directed primer"). The amplified mixture thus obtained is then analysed, for instance based upon the differences in length of the amplified fragments obtained. Usually, this is carried out using conventional gelelectrophoresis/autoradiography to provide a fingerprint, which can then be analysed for the presence or absence of the specific polymorphic fragments. Generally, these known techniques differ in the primers combinations used to amplify the nucleic acid fragments, as will be further discussed hereinbelow. For a description of some of these known techniques, reference is made to WO 96/22388 by applicant; EP 0 804 618; Wu et al., *Nucl. Acids Research*, 1994, Vol.22., No.15, 3257–3258; Matsumoto et al, *Mam-*

*malian Genome* 9, 531–535 (1998); as well as to some of the further prior art mentioned therein. In the state of the art, a method for analysing nucleic acid sequences for microsatellite-associated polymorphisms or markers therefor, involving the use of a combination of both a microsatellite-based RAMP-primer and an AFLP-primer has not yet been disclosed or suggested.

For instance, Wu et al. describe the use of a RAMP-primer in combination with an RAPD-primer. Such an RAPD primer differs from an AFLP-primer in that it is not (intended to be) complementary to an adapter. Thus, in the method of Wu et al, the target DNA will usually also not contain an adapter.

EP 0 804 618 describes a technique referred to as "SAMPL". This technique involves the use of two primers, one of which may inter alia be an AFLP-primer, and the other of which—the microsatellite-directed primer also referred to as the "SAMPL"-primer—is (intended to be) complementary to a so-called "compound repeat SSR", which is an SSR comprising at least two different parts with each part comprising a different repeated sequence (e.g. 5'-CTCTCTCTGAGAGAGA-3'). However, even though the latter primer is intended to be complementary to a microsatellite (albeit a specific type of microsatellite) and even though the primer may also be considered to comprise a 3'-part and a 5'-part, the microsatellite-directed primer used in EP 0 804 618 differs from the RAMP-primer used in the invention.

Thus, it is an object of the invention to provide improved or alternative methods for identification and analysis of microsatellite-based polymorphisms and markers based thereon. Particularly it is an object of the invention to provide such methods involving the use of a combination of both a microsatellite-based RAMP-primer and an AFLP-primer.

DESCRIPTION OF THE INVENTION

In the description hereinbelow and unless indicated otherwise, essentially the same terms will be used as in the above-mentioned art. For instance, unless indicated otherwise, the following terms will have their usual meaning from the references indicated above:
  "simple sequence repeats" or "SSRs"; "simple sequence length polymorphisms"; "dinucleotide, trinucleotide, tetranucleotide or pentanucleotide repeats"; "simple tandem repeats" and/or "microsatellites" (which terms should be considered equivalent and interchangeable);
  "tandem repeat";
  "simple SSR"; "compound SSR"; "perfect SSR"; "imperfect SSR"; "perfect compound SSR" (vide for instance page 8 of EP 0 804 618);
  "non-degenerate"; "(fully or partially) degenerate"; "arbitrary" (vide in particular EP 9 804 618, page 10);
  "Random amplified microsatellite polymorphisms" or "RAMP"; and "RAMP-primer" (vide for instance Wu et al);
  "anchor" or "anchor region" (vide for instance page 8 of EP 0 804 618);
  "AFLP", "AFLP-primer", "adapter", "selective bases/nucleotides", "frequent cutter", "rare cutter" (vide for instance EP 0,534,858)
  "RAPD primer" (vide for instance page 3 of EP 0 804 618).

It is a general object of the invention to provide a method for the identification and/or analysis of nucleic acid sequences. In particular, it is an object of the invention to provide a method that can be used to analyse a nucleic acid sequence for one or more microsatellite-associated polymorphisms/markers. Generally, the above objects are achieved by amplifying the nucleic acid—and in particular one or more adapter-ligated restriction fragments generated from the nucleic acid—with a combination of a RAMP-primer and an AFLP-primer; and then analysing the amplified mixture thus obtained. Thus, in its broadest scope, the invention comprises the use of a RAMP-primer in combination with an AFLP-primer in analysing nucleic acid sequences.

In particular, the invention comprises the use of a RAMP-primer in combination with an AFLP-primer in analysing a nucleic acid sequence for (the presence or absence of) microsatellite-associated polymorphisms/markers.

By "microsatellite-associated polymorphism or marker" is generally meant any polymorphism or marker that is caused by, and/or that is related to, the presence and/or absence of a microsatellite in the nucleic acid, e.g. at one or more specific sites in the nucleic acid. Usually, in the invention, such a presence or absence, respectively, of a microsatellite at such site(s) in the nucleic acid to be analysed (or for instance the presence of a different microsatellite at such site(s) will lead to the generation of different polymorphic fragments, for instance bands that correspond to amplified fragments of different size and/or length (so-called "fragment length polymorphisms").

The method of the invention is schematically illustrated in the non-limiting FIG. 1, in which the RAMP-primer is indicated as (1), the nucleic acid to be amplified—also referred to hereinbelow as the "target DNA"—is indicated as (2), and (the sequence of) a microsatellite present in/on the target DNA is indicated as (3). As schematically shown in FIG. 1, the RAMP-primer (1) is (intended to be) complementary to that part of the sequence of the target DNA (2) that at least comprises the 5' part of the microsatellite repeat sequence (3), so as to allow—e.g. during amplification—the extension of the RAMP-primer (1) in the 3'-direction along the target DNA (2), which serves as a template for the extension of the RAMP-primer (1). As also schematically shown in FIG. 1, the RAMP-primer (1) may be considered to comprise essentially two parts, i.e. a 3'-part and a 5'-part, indicated in FIG. 1 as (4) and (5), respectively. The 3'-part (4) of the RAMP-primer (1) is (intended to be) essentially complementary to (the sequence of) the microsatellite (3). The 5'-part (5) of the RAMP-primer (1) is (intended to be) complementary to the (same number of) bases/nucleotides that, in the target DNA (2), are directly adjacent to the 3'-end of the microsatellite (3). The nucleotides of the 5'-part (5) of the RAMP-primer—which constitute the so-called "anchor (region)" of the RAMP-primer (1) and thus will also be referred to hereinbelow as the "anchor nucleotides"—are indicated as (6) in FIG. 1. The AFLP-primer used in the invention, indicated as (7) in FIG. 1, is essentially the same as a conventional AFLP-primer, in that it is (at least) complementary to (the sequence of) an adapter, indicated as (8) in FIG. 1, that has been inked to the target DNA (2), so as to allow—e.g. during amplification—the extension of the AFLP-primer (7) in the 3'-direction along the target DNA (3), which serves as a template for the extension of the AFLP-primer (7). Most preferably, as in AFLP®, the primer contains, at its 3'-end, a number of so-called "selective bases/nucleotides"—indicated as (9) in FIG. 1—that are (intended to be) complementary to (same number of) bases/nucleotides that, in the target DNA (2), are directly adjacent to the 3' end of the adapter (8). Using the RAMP-primer (1) and the AFLP-primer (7), the target nucleic acid (2) is amplified, e.g. as indicated by the arrows in FIG. 1. In particular, during the amplification, the RAMP-primer (1) will be extended along one strand of the (double stranded) target DNA (2) and the AFLP-primer will be extended along the other strand of the (double stranded) target DNA (2), e.g. so as to allow for efficient/exponential amplification. The mixture of amplified products/fragments thus obtained may then be analysed, e.g. by detecting/visualising at least one, and up to essentially all, of the amplified products/fragments, e.g. as further described hereinbelow.

Accordingly, if—for instance—there is a CT/GA type repeat in an AFLP fragment generated with for example EcoRI and TaqI as restriction enzyme combination, according to the invention the fragment may be amplified exponentially and then visualised in either of two ways, i.e. 1) using a RAMP primer directed against the CT repeats in combination with a TaqI (of EcoRI) AFLP primer; or 2) using a RAMP primer directed against the GA repeats in combination with an EcoRI (of TaqI) AFLP primer. The length(s) of the amplified products obtained in 1) and 2) respectively will depend upon the "distance" of the repeat to the respective restriction site(s).

The prior art does not describe or suggest a method for analysing microsatellite-associated polymorphisms or markers involving the use of both a RAMP-primer and an AFLP-primer has not yet been. For instance, Wu et al. describe the use of a RAMP-primer in combination with an RAPD-primer. Such an RAPD primer differs from an AFLP-primer in that it is not (intended to be) complementary to an adapter. Thus, in the method of Wu et al, the target DNA will usually also not contain an adapter.

EP 0 804 618 describes a technique referred to as "SAMPL". This technique involves the use of two primers, one of which may inter alia be an AFLP-primer, and the other of which—the microsatellite-directed primer also referred to as the "SAMPL"—primer—is (intended to be) complementary to a so-called "compound repeat SSR", which is an SSR comprising at least two different parts with each part comprising a different repeated sequence (e.g. 5'-CTCTCTCTGAGAGAGA-3'). However, even though the latter primer is intended to be complementary to a microsatellite (albeit a specific type of microsatellite) and even though the primer may also be considered to comprise a 3'-part and a 5'-part, the microsatellite-directed primer used in EP 0 804 618 differs from the RAMP-primer used in the invention. In particular, in the microsatellite-directed primer of EP 0 804 618, both the 3'-part of the primer as well as the 5'-part of the primer is (intended to be) complementary to the microsatellite, i.e. the sequence of the compound repeat SSR. In particular, the 3'-part is (intended to be) complementary to a first repeat/part of the compound repeat SSR, whereas the 5'-part is (intended to be) complementary to a second repeat/part of the compound repeat SSR.

Thus, the microsatellite-directed primers used in EP 0 804 618 will themselves essentially consist only of repeats of dinucleotides, trinucleotides, etc. Accordingly, these primers will essentially not contain bases/nucleotides that are (intended to be) complementary to bases/nucleotides that lie immediately adjacent to the 5' boundary of (the sequence of) the microsatellite as present in/on the target DNA; or at least the presence of such nucleotides is not required. In this respect, EP 0 804 618 inter alia states (page 11, lines 15–18): "Additionally, PCR primers representing these compound SSR sequences are self-anchoring, such that the 5'-most repeat serves as. the anchor for primer extension by the 3'-most of the two repeats, thus obviating the need to incorporate into these primers any additional degenerate or fixed sequences as 5' or 3' flanking regions". As an alternative for the use of primers that are complementary to compound repeat SSRs, EP 0 804 618 on page 14, lines 49–56 also describes the use of primers of which the 3'-part corresponds to a simple SSR or microsatellite, whereas the 5'-part of such a primer "contains 3 to 5 fully or partially degenerate nucleotides, which serve to anchor the primer adjacent to a microsatellite in the targeted genome".

In this respect, as indicated on page 10 of EP 0 804 618: ""Fully degenerate" indicates the presence of an equal mixture of the four possible nucleotide bases (A, G, C or T) at a particular nucleotide position, partially degenerate indicates the presence of only two or three of the four possible bases at a particular base position."

In contrast, the 5'-part of the primer(s) used in the invention contain(s)—in the terms used in EP 0 804 618—only "non-degenerate" bases/nucleotides, which refers to "the occurrence of a single, specified nucleotide type at a particular position or at multiple specified positions in the linear ordering of nucleotides". A particular advantage of the use of such defined (i.e. completely non-degenerate) anchor sequences is that RAMP primers directed at the same repeat motif (identical 3' sequence of the primer) but with different anchor sequences (5' prime sequence of the primer) can be used to target completely distinct subsets or partially overlapping subsets of microsatellites. This characteristic of the invention increases dramatically the number of different microsatellite repeats that can be identified compared to the SAMPL technique described in EP 0 804 618. Thus the resolving power of the method of the invention to visualise microsatellites compares favourably to that of the art described in EP0 804 618.

Also, according to the definitions given in EP 0 804 618 "Any non-degenerate nucleotide position can carry an intended base (either A, G, C or T) that is known for example to correspond to a given template site, or it can carry an arbitrarily chosen base, which will correspond to a target site that is not known a priori". Both these possibilities are also incorporated within the scope of the present invention, with the use of arbitrarily chosen bases/nucleotides in the RAMP-primers of the invention usually being preferred.

However, according to one particular embodiment, if the "anchor" sequences in the RAMP-primer are non-arbitrary, the anchor sequences do not form or correspond to a repeat motif (or in other words, the RAMP-primer used does not correspond to a "SAMPL"-primer. i.e. as used in EP 0 804 618).

Thus, in a first aspect, the invention relates to the use of (the combination of) a RAMP-primer and an AFLP-primer in amplifying a nucleic acid sequence (herein also referred to as the "target nucleic acid"). In this aspect of the invention, and with reference to FIG. 1, the target nucleic acid usually will comprise a adapter (8) and a further nucleic acid sequence, indicated as (11) in FIG. 1, to which the adapter has been ligated. In particular, in this aspect of the invention, the further nucleic acid sequence (11) present in the target nucleic acid (2) will be a restriction fragment. For instance, the further nucleic acid (11) can be a restriction fragment derived from a starting DNA—including but not limited to genomic DNA, cDNA or recombinant DNA such BAC DNA, cosmid DNA or plasmid DNA—by restriction with a restriction endonuclease (as further described hereinbelow), although the invention in its broadest sense is not limited thereto.

Also, the target nucleic acid (2) will usually be a DNA sequence, and in particular a double stranded DNA sequence, although the invention in its broadest sense is again not limited thereto.

The target nucleic acid (2) may comprise a single adapter (8) but usually comprises two adapters (8), e.g. each ligated to one end of the restriction fragment (11) present in the target nucleic acid. Also, when two adapters (8) are present, they may be the same or different.

Also, the target nucleic acid (2) may be part of a mixture of such target nucleic acids. For instance, when the target nucleic acid comprises a restriction fragment ligated to an adapter, it may be part of a mixture of such adapter-ligated restriction fragments. Such a mixture may for instance be obtained by ligating a adapter to a mixture of restriction fragments, which may be carried out in a manner known per se, for instance as described in the above prior art, including but not limited to EP 0 534 858.

Optionally, such a mixture of target nucleic acids may (already) have been subjected to a (pre)amplification step, i.e. prior to the amplification with the RAMP-primer and the AFLP-primer. This may also be/have been a "selective" pre-amplification for reducing the complexity of the mixture. For instance, when the target nucleic acid(s) (2) contain two adapters (8), such a selective pre-amplification may be carried out as a conventional AFLP-pre-amplification, for which reference is made to EP 0 534 858.

Besides the adapter, the target nucleic acid (2) preferably also contains (or is at least suspected to contain) a microsatellite, or otherwise the target nucleic is at least part of a mixture of such target nucleic acids of which a target nucleic acid contains (or is suspected to contain) a microsatellite; and in particular a microsatellite to which the RAMP-primer (1) can and/or is intended to hybridise.

The microsatellite (3) can be any microsatellite/SSR or sequence corresponding thereto, and in particular can be any microsatellite/SSR that may occur naturally in the genome of an eukaryote. Some non-limiting examples of (nucleotide sequences of) such microsatellites are described in the above-mentioned art.

As such, the microsatellite/SSR may for instance be a simple SSR or a compound SSR; and/or may be a perfect SSR and/or an imperfect SSR; or any combination thereof Preferably, the microsatellite is a multi-allelic SSR, although the invention in its broadest sense is not limited thereto.

The RAMP-primer (1) will be at least such that, when (the sequence of) a microsatellite (3) to which the RAMP-primer (1) is complementary is present in the target nucleic acid, it is capable of hybridising with the microsatellite (3) so as to allow extension of the RAMP-primer (1) along the target nucleic acid (2)

Usually, a RAMP-primer (1) used in the invention will contain a total of between 8 and 20 nucleotides, and in particular between 12 and 16 nucleotides.

Of these, between 4 and 10 nucleotides, and in particular between 6 and 8 nucleotides will form part of the 3'-part (4) of the RAMP-primer (1)—i.e. the part that is complementary to (the repeat motif of) the microsatellite—and between 4 and 10 nucleotides, and in particular between 6 and 8 nucleotides will form part of the 5'-part (5) of the RAMP-primer (1), i.e. the anchor region.

Thus, with reference to the symbols used on pages 9 and 10 of WO 96/22388, a RAMP-primer suitable for use in the invention may for example be schematically represented by the formula

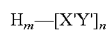

$H_m$—$[X'Y']_n$ in which H represents an anchor nucleotide, arbitrarily selected from the four bases A,T, C or G; "m" is a whole number between 1 and 10, preferably between 3 and 8; X'Y' represents a simple sequence repeat unit of 1, 2, 3 or 4 nucleotides intended to be complementary to a simple sequence repeat XY unit present in a microsatellite in the target nucleic acid; $[X'Y']_n$ represents a simple sequence repeat of n repeat units; and "n" is a whole number between 2 and 10, preferably between 3 and 6. Thus, in the above formula, and with reference to FIG. 1 and the description hereinabove, $H_m$ represents 5'-part (5) of the RAMP-primer, whereas $[X'Y']_n$ represents the 3'-part (4).

Thus, usually, in the invention, (the 3'-part of) the RAMP primer will represent a simple sequence repeat $[X'Y']_n$.

Also, with reference to the terms used in EP 0 804 618, the anchor nucleotides that form the 5'-part (5) of the RAMP-primer will be "non-degenerate" nucleotides, and preferably are "arbitrary" non-degenerate nucleotides. As mentioned above, (the use of) such microsatellite-directed primers is not disclosed by EP 0 804 618.

The AFLP-primer (7) will be essentially the same as a conventional AFLP-primer, e.g. as described in EP 0 534 858, and will generally contain a constant region—indicated as (10) in FIG. 1—and one or more selective nucleotides at the 3'-end thereof.

Also, the AFLP-primer (7) is most preferably essentially complementary to at least one of the adapters (8) used, e.g. so as to allow extension of the AFLP-primer (7) along the target nucleic acid (2).

Preferably, the AFLP-primer (7) will contain a total of between 15 and 50 nucleotides, and in particular between 18 and 30 nucleotides. Also, preferably, the AFLP-primer (7) will contain between 1 and 6, preferably between 1 and 3 selective nucleotides.

The amplification of the target nucleic acid (2) with the RAMP-primer (1) and the AFLP-primer (7) may be carried out under conditions known per se, including but not limited to conditions known per se for amplification using RAMP-primers and/or conditions known per se for amplification using AFLP-primers. Such conditions are for instance described in the above-mentioned prior art (e.g. Wu et al. for RAMP-primers and EP 0 534 858 for AFLP-primers) and some non-limiting examples of suitable conditions are also given in the Experimental Part hereinbelow. It is envisaged that based upon these disclosures, the skilled person will be able to select (a range of) optimal conditions for the amplification of a given (mixture of) target nucleic acid(s) with a given combination of RAMP-primer and AFLP-primer.

Usually, the amplification is carried out using only one RAMP-primer as described above and only one AFLP-primer as described above, although the invention in its broadest sense is not limited thereto.

Also, the RAMP-primer and the AFLP-primer are preferably such that they allow for efficient/exponential amplification. In this respect, it should be noted that, when the target nucleic acid is part of a mixture of such target nucleic acids, in the amplification step usually more than one of the target nucleic acids that are present is the mixture will be amplified, i.e. to provide a mixture of amplified fragments.

After the amplification with the RAMP-primer and the AFLP-primer, the amplified nucleic acid thus generated is detected. For instance, when the amplification step has provided a mixture of amplified fragments as described hereinabove, one or more—and up to essentially all—amplified fragments present in the mixture may be detected.

The detection may be carried out using any technique known per se for the detection of an amplified nucleic acid/fragment and/or for analysing a mixture of amplified nucleic acids/fragments. Suitable techniques are described in the above-mentioned art and for instance include techniques in which the amplified fragments are separated and visualised (e.g. gelchromatography and autoradiography to provide a fingerprint); (other) detection techniques based upon the mass and/or the size of the amplified fragments; and techniques involving the hybridisation of one or more of the amplified fragments to a complementary nucleotide sequence (in which the complementary nucleotide sequence may for instance be immobilised on a suitable carrier, e.g. as part of an array of such nucleotide sequences) followed by detection of such hybridisation events. Generally, these detection techniques will be such that they allow for the detection of polymorphisms, as further described below.

In another aspect, the invention relates to a method for analysing a nucleic acid sequence, the method at least comprising the steps of:
(a) amplifying a restriction fragment generated from the nucleic acid to be analysed, in which the restriction fragment has been ligated to a adapter, with a RAMP-primer and a AFLP-primer to provide a amplified nucleic acid sequence;

and optionally comprising the further step of:
(b) detecting at least one of the amplified nucleic acid sequences thus obtained.

More specifically, this aspect of the invention relates to a method for analysing a nucleic acid sequence, the method comprising the steps of:
(a) restricting the starting nucleic acid with a restriction endonuclease to provide a mixture of restriction fragments;
(b) ligating the restriction fragments thus obtained to a adapter;
(c) amplifying the mixture of adapter-ligated restriction fragments thus obtained with a RAMP-primer and a AFLP-primer to provide a mixture of amplified restriction fragments;

and optionally comprising the further step of:
(d) detecting at least one of the amplified restriction fragments thus obtained.

In the above aspects of the invention, the (starting) nucleic acid is preferably a DNA sequence, more preferably a double stranded DNA sequence.

In particular, the starting nucleic acid can be a nucleic acid that contains (or is at least suspected to contain) a microsatellite to which the RAMP-primer used can and/or is intended to hybridise. For instance, the starting nucleic acid sequence can be genomic DNA, cDNA; and in particular eukaryotic genomic DNA, cDNA or (a mixture or a library of) recombinant DNA clones, e.g. derived from a plant, animal or a human.

For instance, the starting nucleic acid can be derived from agronomically important crops such as wheat, barley, maize, tomato, pepper, lettuce, rice, soybean etc.; from animals such as such as mouse, rat, pig, chicken, fish, etc.; and/or from humans.

In the restriction step a), the starting nucleic acid is restricted with a restriction endonuclease, which may be any suitable restriction endonuclease, including but not limited to those mentioned below.

In particular, the starting nucleic acid may be restricted with two different restriction endonucleases. For instance, the starting nucleic acid may be restricted with one "frequent cutter" restriction endonuclease, which serves the purpose of reducing the size of the restriction fragments to a range of sizes which are amplified efficiently; and one "rare cutter" restriction endonuclease, which serves the purpose of targeting rare sequences. For both, reference is made to for instance EP-A-0 534 858 and EP-A-0 721 987 by applicant, incorporated herein by reference. The skilled person will understand that the recognition sequence of a frequent cutter usually has no more than four bases that provide selectivity, whereas a rare cutter usually has at least six selective bases in its recognition sequence. However, whether a given enzyme functions as a rare or a frequent cutter also depends on the base composition of its recognition site and the overall base composition of the sample DNA to be digested. Thus, a four-cutter with only G's and C's in its recognition site may act as a rare cutter on AT-rich DNA. Therefore a frequent cutter is understood to be an restriction enzyme that upon restriction of a given sample DNA produces restriction fragments the majority of which is less than 1 kb in length, whereas the majority of fragments produced with a frequent cutter is larger than 1 kb in length. Some non-limiting examples of suitable frequent cutter enzymes are MseI, TaqI, and MboI (Sau3A). Some non-limiting examples of commercially available rare cutters are PstI, HpaII, MspI, ClaI, HhaI, EcoRII, BstBI, HinP1, MaeII, BbvI, PvuII, XmaI, SmaI, NciI, AvaI, HaeII, SalI, XhoI and PvuII, of which PstI, HpaII, MspI, ClaI, EcoRI, BstBI, HinP1 and MaeII are preferred.

After the restriction step a), the restricted fragments thus obtained are ligated to an adapter. This adapter will be essentially the same as the adapter(s) used in conventional AFLP, for which reference is again made to the prior art relating to AFLP mentioned above. As in conventional AFLP, the adapter used is most preferably such that it is suitable for use with at least one of the restriction enzymes used in the restriction step a). For instance, when the starting DNA is restricted with two restriction endonucleases (e.g. a frequent cutter and a rare cutter) preferably also two adapters are used, each suitable for use with one of the restriction endonucleases.

After the adapter has been ligated with to the restriction fragments, the mixture of adapter-ligated restriction fragments thus obtained may then (directly) be amplified in step c) with the RAMP-primer and the AFLP-primer. However, as already indicated above, prior to the amplification step c), the (adapter-ligated) restriction fragments may first be subjected to a pre-amplification, and in particular a selective pre-amplification for reducing the complexity of the fragment mixture. For instance, such a selective pre-amplification may be carried out analogous to a selective pre-amplification known per se from AFLP, for which reference is again made to the prior art related to AFLP mentioned above.

More generally, the restriction step a), the ligation step b) and any pre-amplification step described above may be carried out in essentially the same manner as the restriction, ligation and amplification steps of conventional AFLP methodology, e.g. according to known AFLP protocols. The subsequent amplification step c) of the adapter-ligated restriction fragments with the RAMP-primer and the AFLP-primer may be carried out as described hereinabove and as illustrated in FIG. 1, in which the adapter-ligated restriction fragments serve as the "target nucleic acid" (2).

Thereafter, the amplified mixture thus obtained is analysed, which is also carried out as described hereinabove. Generally, these detection techniques will be such that they allow for the detection of polymorphisms, e.g. detectable signals that are unique for the starting nucleic acid. For instance, such a unique detectable signal may be a unique band in a fingerprint or a unique hybridisation event/signal on an array; or the lack of such a band or hybridisation signal. For this purpose, the detectable signal(s) generated for a specific starting nucleic acid will usually be compared to the detectable signal(s) obtained for one or more related starting nucleic acid(s) under essentially the same conditions (e.g. the use of the same restriction enzymes, adapters, pre-amplification (if any), RAMP-primer, AFLP-primer and detection technique), for instance by comparing fingerprints and/or hybridisation signals/patterns on a given array. Such related starting nucleic acids may for instance have derived from the same individuals and/or from one or more closely related individuals (e.g. from the same family, genus, species or even variety). For instance, one or more such related starting nucleic acids may be used/incorporated as reference sample(s) in the method of the invention, in which case the results for the starting nucleic acid sequence and the reference sample(s) may be directly compared. Alternatively, the results obtained for a given starting nucleic acid may be compared to results generated earlier for one or more related nucleic acid sequences, which may for instance be part of a database.

Again, such detection techniques and techniques for analysing/comparing the results obtained will be essentially analogous to the techniques used to analyse the results obtained using AFLP, for which again reference is made to the prior art related to AFLP mentioned above. Thus, from the above, it will be clear that the method of the invention may conveniently be carried out analogous to a conventional AFLP-amplification, in which for the "main" amplification a combination of one AFLP-primer and one RAMP-primer is used, instead of two AFLP-primers.

Also, as in conventional AFLP, the selective nucleotides (9) of the AFLP-primer (7) may be selected arbitrarily. Also, in the RAMP-primer (1), both the anchor nucleotides (6) that form the 5'-part (5) of the RAMP-primer, as well as the specific repeat sequence that forms the 3'-part (4) of the RAMP-primer may be arbitrarily selected, in which the repeat sequence may be chosen arbitrarily from any and all nucleotide sequences that are complementary to the sequence of a naturally occurring microsatellite. In particular, the repeat sequence that forms the 3'-part (4) of the RAMP-primer (1) may be arbitrarily selected from any and all nucleotide sequences that are complementary to the sequence of a microsatellite that may be present in the starting DNA. In this respect, it should be noted that, generally, any given starting DNA will contain a large number of different microsatellites, e.g. up to thousands or more. Thus, as with conventional AFLP, the method of the invention does not require any prior knowledge of the sequence to be analysed, nor the use of any specifically designed primers.

Also, the invention may allow the detection of microsatellite-associated polymorphisms/markers in conjunction with AFLP-markers, and thus provide a very powerful (combined) technique for the analysis of a starting nucleic acid for both these types of highly informative genetic markers. However, as with conventional AFLP, it may be that some (combinations of) specific AFLP-primers and RAMP-primers may provide, for a specific starting DNA, more informative results (e.g. more polymorphic fragments) than other combinations, and that some combinations may even provide no informative results at all. Nevertheless, based upon the disclosure herein, the skilled person will be able to provide one or more suitable combinations of a RAMP-primer and an AFLP-primer for analysing a specific starting DNA according to the method of the invention, optionally after some preliminary experiments and/or a limited degree of trial and error.

In principle, the method of the invention can be used for any application for which a microsatellite-associated polymorphic marker can be developed or used. Such applications include, but are not limited to, all uses described in the above-mentioned art, e.g. in WO 96/22388 by applicant and/or in EP 0 804 618, such as in genotyping, genetic mapping, genetic profiling and DNA-identification techniques, e.g. to identify a specific species, subspecies, variety, cultivar, race or individual, to establish the presence or absence of a specific inheritable trait and/or of a gene; or to determine the state of a disease.

Generally the methods of the invention may provide the following advantages (e.g. compared to the prior art methods for detecting microsatellite-associated polymorphisms mentioned hereinabove:

efficient targeting of a large proportion of microsatellites present in the genome, particularly those with simple repeat motifs.

highly reproducible fingerprint patterns due to excellent reproducibility of the AFLP technique compared to other techniques.

A particularly envisaged application comprises for instance amplification of several highly informative microsatellites in combination with AFLP markers in multiplex form in a single amplification reaction.

According to the invention one or more of the microsatellite-associated markers identified using the method of the invention are (further) developed into "classical" PCR-test. This may for instance be carried out by a method as schematically illustrated in the non-limiting FIG. 2.

In one aspect, the present invention accordingly pertains to a method for the determination of PCR-primers, PCR-primers, the use thereof in the development of a PCR-assay and to the use of (a combination of) a RAMP primer and a AFLP® primer in the development of PCR-primers. More in particular, the present invention provides a method for the development of PCR-primers that are suitable for use in a conventional PCR-test. More in particular, the present invention provides a method wherein microsatellites determined by a recently developed method based on AFLP®-technology can be converted into conventional SSR-assays based on flanking PCR-primers.

The present invention provides technologies that allow the conversion of the microsatellite associated markers into primers that can be used in a conventional PCR-test. The present invention also provides for PCR-primers, based on AFLP®-technology associated with the identification of microsatellites. Further the invention provides for primers that can be used in SRR-assays based on PCR technology.

Generally, this method involves the identification of a microsatellite-associated polymorphic fragment, e.g. as described hereinabove. This polymorphic fragment 11 (e.g. a fragment amplified using the combination of a RAMP-primer and an AFLP-primer for the first restriction enzyme used for AFLP template preparation) and optionally one or more alleles thereof) is then isolated (e.g. cut out of the gel obtained after gelelectrophoresis) and sequenced (step 1 in FIG. 2). Based upon the sequence of the polymorphic fragment(s) thus obtained, a suitable PCR-primer is selected/designed from the sequence flanking the microsatellite repeat sequence at the 3' end. Next, this PCR primer, in combination with an AFLP primer corresponding to the second enzyme used for AFLP template preparation is used to amplify a fragment that contains the microsatellite and the 5' flanking sequence, which is not included in the polymorphic fragment initially chosen for sequencing (step 2). From this 5' flanking sequence a suitable second PCR primer is selected/designed (step 3), which together with the first PCR primer matching the 3' flanking sequence is used in a conventional PCR-detection, e.g. on the starting DNA (step 4).

In one aspect, the invention pertains to a method for providing a PCR primer comprising the steps of identification of a microsatellite-associated polymorphic fragment amplified by the combined use of a RAMP primer and an AFLP® primer for the first restriction enzyme used for AFLP® template preparation, sequencing the fragment, designing and synthesising a first PCR-primer for the sequence flanking the microsatellite repeat sequence at the 3' end; optionally amplifying a fragment comprising the microsatellite and at least part of the 5'-flanking sequence using the first PCR-primer and a second AFLP® primer used for AFLP® template preparation, and optionally designing and synthesising a second PCR-primer for the sequence flanking the microsatellite repeat sequence at the 5' end.

The method according to the invention involves the identification of a microsatellite associated polymorphic fragment, e.g. as described hereinbefore. This polymorphic fragment (e.g., a fragment amplified using the combination of a RAMP primer and an AFLP-primer for the first restriction enzyme used for AFLP template preparation and optionally one or more alleles thereof) is isolated (e.g. cut out of the gel obtained after gelelectrophoresis) and sequenced (step 1 in FIG. 2). For the purpose of sequencing, the gel-excised fragments may be cloned in convenient sequencing vectors. Alternatively, the gel-excised fragments are re-amplified in a PCR using the RAMP-primer used in the original amplification, and a modified version of the AFLP-primer used in the original amplification. The modified AFLP-primer preferably contains an additional sequence at its 5'-end that may conveniently be used for priming subsequent sequencing reactions. A convenient example of such additional sequence for priming sequencing reactions is sequence of the universal M13 sequencing primer. Based on the sequence of the polymorphic fragment(s) thus obtained, a suitable PCR-primer is selected/designed from the sequence flanking the microsatellite repeat sequence at the 3'-end. Next, this PCR-primer, in combination with an AFLP-primer corresponding to the second enzyme used for AFLP template preparation, is used for the amplification a fragment that contains the microsatellite and an additional 5'-flanking sequence, that is downstream from the microsatellite with respect to the first PCR primer. This additional 5'-flanking sequence was not present in the polymorphic band initially chosen for sequencing (step 2 in FIG. 2). The additional 5'-flanking sequence is used as basis for the design of a suitable second PCR-primer (step 3 in FIG. 2), which together with the first PCR primer matching the 3'-flanking sequence is suitable for use in a conventional PCR-detection, e.g. on the starting DNA (step 4 in FIG. 2).

The present invention provides for a reliable and powerful method for the generation of PCR primers. The PCR primers obtained according to the invention preferably are suitable for use in conventional PCR-technology and more preferably are suitable PCR primers for use in conventional SSR-assays based on flanking PCR primers, whereby the SSR's have been identified using microsatellite-AFLP® technology. Hence, microsatellite AFLP® provides a valuable technique for rapid and reliable identification of highly polymorphic SSRs. A further advantage is that these SSRs can be identified randomly across the genome, which is a distinct advantage of the present invention over the conventional techniques, such as exemplified by library-based SSR identification.

In a preferred embodiment of the invention, the steps indicated as optional are also included in the method. It is hence preferred that a second PCR primer is designed for the development of an SSR-assay based on conventional PCR. The skilled person will appreciate that alternative methods exist for obtaining the additional flanking sequence on the basis of which the second PCR primer will be designed, in addition to the method based on the second AFLP-primer as specifically disclosed in the present application. Such methods e.g. include sequencing of fragments obtained by inverse PCR.

A flanking sequence in terms of the present invention refers to a sequence adjacent to a microsatellite repeat sequence. The length of a flanking sequence will usually be defined by the distance between a microsatellite repeat sequence and another sequence, for instance a sequence designated or suitable as PCR-primer or AFLP®-primer and the like. The length of a flanking sequence generally varies between 0 and 500 nucleotides, preferably up to 250, more preferably up to 150 and most preferably up to 100 nucleotides. The upper limit will generally be governed by factors such as the resolution of the gel and the length of the microsatellite fragment.

In a further aspect, the invention pertains to a method for the determination of a PCR-primer, comprising the steps of:
  restricting a nucleic acid sequence with a restriction endonuclease to provide a mixture of restriction fragments;
  ligating the restriction fragments thus obtained to a adapter;
  amplifying the mixture of adapter ligated restriction fragments thus obtained with a RAMP-primer and a first AFLP®-primer to provide a mixture of amplified restriction fragments;
  detecting at least one of the amplified restriction fragments thus obtained;
  identifying a microsatellite-associated polymorphic fragment or band;
  determining the sequence of the polymorphic fragment or band;
  designing a first PCR-primer for the sequence flanking the microsatellite repeat sequence at the 3' end;
  optionally amplifying a fragment comprising the microsatellite and at least part of the 5'-flanking sequence using the first PCR-primer and a second AFLP®-primer;
  optionally designing a second PCR-primer for the sequence flanking the microsatellite repeat sequence at the 5' end.

The invention further relates to primers obtainable by the present invention in the development of an assay, preferably for the analysis of microsatellites. The invention further relates to the use of (the combination of) a RAMP primer and an AFLP® primer in the development of PCR-primers, preferably suitable for use in SSR-assays.

The polymorphic fragment which is used to determine a suitable PCR-primer is preferably derived from genomic DNA; and in particular eukaryotic genomic DNA or (a mixture or a library of) recombinant DNA clones e.g. derived from a plant, animal or human being. In a further embodiment, the polymorphic fragment is derived from to agronomically important crops such as for instance wheat barley, maize tomato, pepper, lettuce, rice or soybean; from animals such as mouse, rat, pig, chicken or fish or from a human being.

The invention also relates to the use of a PCR-primer according to the present invention in the development of an assay, preferably for the analysis of microsatellites (i.e. an SSR-assay), and to a kit comprising means for obtaining a PCR-primer according to the invention, as well as to a kit comprising a PCR-primer according to the invention.

Furthermore, one or more of the microsatellite-associated polymorphic fragments identified by the method of the invention is isolated and optionally sequenced, and is used to generate a nucleotide sequence representative for the microsatellite-associated marker for use in—for instance— an array for the analysis of nucleic acid sequences. Such arrays and their preparation are known per se in the art, for instance from applicants pending application PCT/NL99/00743 entitled "array and method for analysing nucleic acid sequences", filed Mar. 12, 1999.

In yet another aspect, the invention relates to the use of a RAMP-primer in the methods described hereinabove. The invention also relates to the use of an AFLP-primer in the methods described hereinabove.

In another aspect, the invention relates to the use of a combination of a RAMP-primer and a AFLP-primer in analysing a nucleic acid sequence. In particular, this aspect of the invention relates to the use of the combination of a RAMP-primer and a AFLP-primer in analysing a nucleic acid sequence for the presence of polymorphisms associated with microsatellites.

Yet another aspect comprises any data generated by the method of the invention, optionally on a suitable data carrier, such as paper or a computer disk. Such data may for instance include the generated DNA-fingerprints (e.g. in the form of a gel) and/or autoradiographs/photographs or other reproductions thereof, as well as (stored) analogous or digital data thereon, e.g. in the form of a database.

The invention also comprises kits for use in the invention, the kits at least comprising a RAMP-primer and an AFLP-primer; and usually also comprising an adapter complementary to the AFLP-primer. These kits can further contain any known component for such kits, including but not limited to components known per se for AFLP kits, such as restriction enzymes (in which case the adapters are preferably suited to be ligated to the restrictes sites generated with the enzyme); a polymerase for amplification, such as Taq-polymerase; nucleotides for use in primer extension; as well as buffers and other solutions and reagents; manuals, etc. Further reference is made to the European patent application 0 534 858, incorporated herein by reference.

DESCRIPTION OF THE FIGURES

FIGS. 1 and 2 are schematic representations of the method of the invention;

FIG. 8 shows the lettuce (SEQ ID Nos.11–13), pickle (SEQ ID Nos. 22–23), maize (SEQ ID Nos.30–31) and pepper (SEQ ID Nos. 34–35) used in the Examples below.

Microsatellites from 3 different crops were converted from microsatellite-AFLP® in to a PCR-based assay and confirmed by amplification from genomic DNA or AFLP re-amplification reactions. Lanes A, B, and C show the microsatellite fingerprint on the left and the PCR products obtained after conversion and amplification from genomic DNA on the right. A: SSR in Tomato. The sample on the left is heterozygous at the microsatellite repeat locus. B: SSR in Barley. C: SSR in Tomato.

EXAMPLES

Example 1

Targeting of Microsatellite Repeat Polymorphisms in Lettuce Using the Combination of an AFLP Primer and a RAMP Primer 1. Description of Biological Materials The biological materials used are lettuce lines Rachel, Vicky, Lianne, Quincy, Thirza, Veraly, Clarion and Ballora.

2. TaqI/MseI AFLP Template Preparation, Pre-amplification and Amplification Using a Selective TaqI AFLP Primer in Combination with a RAMP Primer AFLP templates prepared using the restriction enzymes TaqI and MseI, and pre-amplification reactions were carried out according to standard procedures described by Vos et al., (Nucleic Acids Research 23: no 21, pp. 4407–4414, 1995; and patent application EP0534858).

Microsatellite-repeat fragment-enriched fingerprints patterns were obtained by carrying out a selective amplification from a 20-fold diluted +0/+0 pre-amplification mixture using the combination of a TaqI AFLP selective +3 AFLP primer and a RAMP primer. The amplification reactions were carried out according to the amplification conditions described by Vos et al and in EP0534858. For the results shown in FIG. 3, RAMP primer 98L76 directed at CT sequences (left hand side of FIG. 3) or RAMP primer 99A54 directed at GA sequences (right hand side of the FIG. 3) were used in combination with AFLP primer TR48. The RAMP primers 98L76 or 99A54 were end-labelled with $^{33}$P and the amplification mixtures were resolved on a standard AFLP (sequence) gel. Gels were processed and exposed to a phosphor-imaging screen as described (Vos et al., 1995) to generate the gel-image.

The sequences of the adapters, AFLP pre-amplification primers and (selective AFLP) amplification primers used are as follows:

```
MseI adapter:
92A18:   5'-GACGATGAGTCCTGAG-3'       (SEQ ID No.1)

92A19:   3'-TACTCAGGACTCAT-5'         (SEQ ID No.2)

MseI + 0 pre-amplification AFLP primer:
M00L:    5'-GACGATGAGTCCTGAGTAA-3'    (SEQ ID No.3)

TaqI (rare) adapter:
96A22:   5'CTCGTAGACTGCGTAC-3'        (SEQ ID No.4)

96A23:   3'-TCTGACGCATGGC-5'          (SEQ ID No.5)

TaqI + 0 pro-amplification AFLP primer:
T00K:    5'-GTAGACTGCGTACCGA-3'       (SEQ ID No.6)

TaqI + 3 selective amplification AFLP primer:
TR48:    5'-GTAGACTGCGTACCGACAC-3'    (SEQ ID No.7)

RAMP amplification primers:
98L76:   5'-GATAAGCGCTCTCTCT-3'       (SEQ ID No.8)

99A54:   5'-GACGGCACGAGAGAGA-3'       (SEQ ID No.9)
```

3. Results

Figure 3:
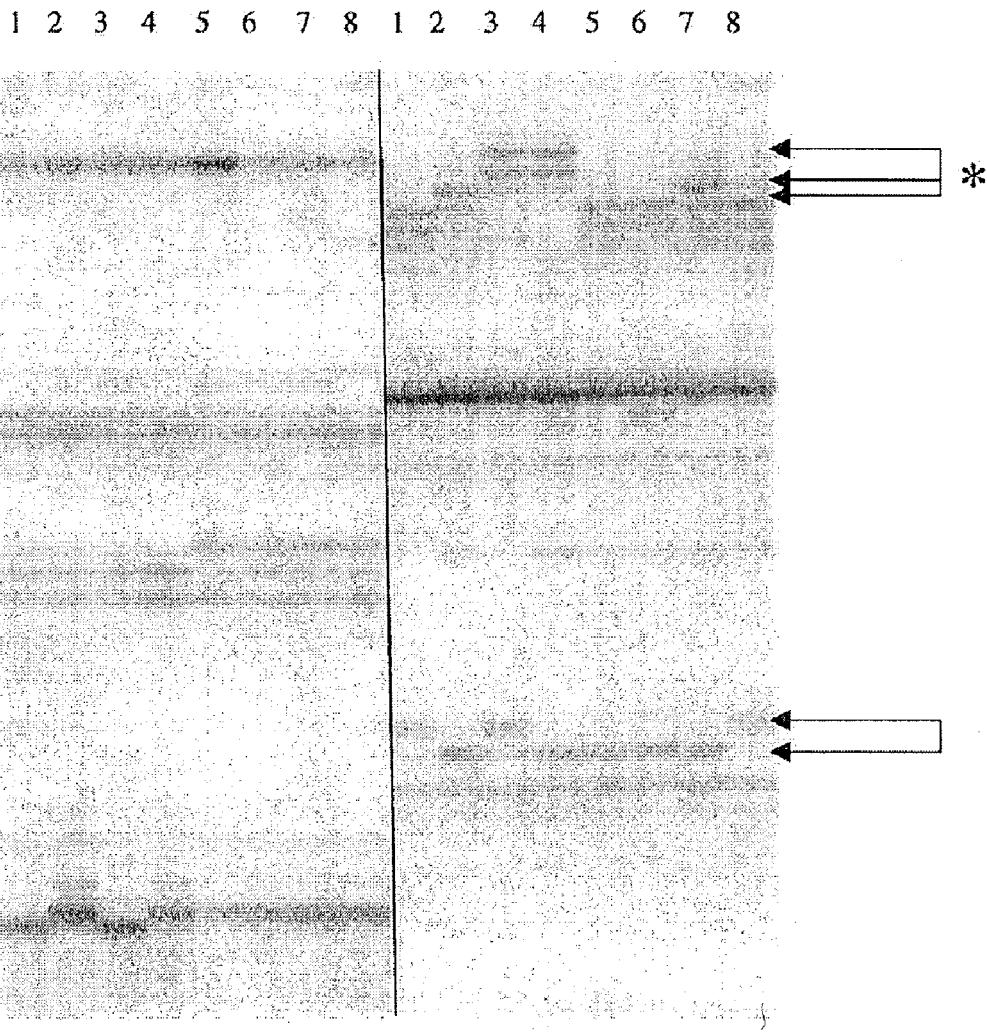
FIG. 3 shows a section in the 200–280 basepairs fragment mobility size range of the fingerprint patterns obtained from lettuce lines Rachel (lane 1), Vicky (lane 2), Lianne (lane 3), Quincy (lane 4), Thirza (lane 5), Veraly (lane 6), Clarion (lane 7) and Ballora (lane 8) using the method of the invention, as further described in Example 1.

FIG. 3 shows a section in the 200–280 basepairs range of the fingerprint patterns obtained after separating the amplified fragments on a sequence gel. The fingerprints on the left hand side of the FIG. 3 were obtained with primer combination 98L76/TR48 from lettuce lines Rachel (lane 1), Vicky (lane 2), Lianne (lane 3), Quincy (lane 4), Thirza (lane 5), Veraly (lane 6), Clarion (lane 7) and Ballora (lane 8), as described above.

The fingerprints on the right hand side of the FIG. 3 were obtained with primer combination 99A54/TR48 from the same lettuce lines, loaded on the gel in the same order.

The bands indicated by arrows may represent alleles of polymorphic microsatellite repeat loci targeted by the RAMP primers used.

4. Confirmation of Targeting a Microsatellite Repeat by Nucleotide Sequencing

The three bands at the top of the right hand part of FIG. 3, amplified using primer combination 99A54/TR48 and indicated by arrows and a star (*) at the side, may represent three alleles of a multi-allelic microsatellite repeat. In order to demonstrate this, the nucleotide sequences of these fragments were determined after excision from the appropriate positions from the sequence gel and eluting the DNA in TE (10 mM Tris, pH 8.0, 1 mM EDTA).

The fragments were re-amplified by PCR from the eluates of Quincy (lane 4), Thirza (lane 5) and Clarion (lane 7), using the primers 99A54 and 99G20 according to standard procedures. The PCR products were purified using Qiagen PCR purification kits (Qiagen). Cycle sequencing was performed using a commercially available dye terminator cycle sequencing kit (ABI), according to instructions provided by the manufacturer.

99G20 (SEQ ID No.10):
5'-AGCGGATAACAATTTCACACAGGACA-CACTGGTATAGACTGCGTACCGA-3'

The resulting three sequences, truncated at the TaqI site, are given in SEQ ID Nos 11–13 and are also shown in FIG. 8, i.e.:

SEQ ID No.11: 260 basepairs, corresponding to "top" of three bands (Quincy)

SEQ ID No.12: 256 basepairs, corresponding to the "middle" of three bands (Clarion)

SEQ ID No.13: 254 basepairs, corresponding to the "bottom" of three bands (Thirza)

5. Conclusion

From FIG. 3 and the inspection of the sequences of SEQ ID NOs 11–13 and FIG. 8 it is apparent that these sequences differ only a the number of CT repeats but are otherwise identical. Furthermore these CT-repeat sequences are flanked by the (inverse complement) sequence of RAMP primer 99A54. These observations prove that a CT microsatellite repeat polymorphism is targeted by using RAMP primer 99A54 in combination with AFLP primer TR48 and that it is very likely that the three bands observed on the fingerprint shown in FIG. 3 represent three alleles of the same microsatellite locus.

Example 2

Targeting of Potential Microsatellite Repeat Polymorphisms in Pickle Using the Combination of an AFLP Primer and a RAMP Primer 1. Description of Biological Materials The biological materials used are the parental lines and six F2 progeny of a pickle mapping population. The parental lines are G421 (indicated by P1 in FIG. 4) and H19 (indicated by P2 in FIG. 4). The F2 progeny used are numbered 001, 002, 003, 004, 005 and 006.

2. EcoRI/MseI Template Preparation and Amplification Using a Selective EcoRI Primers in Combination with a RAMP Primer.

Figure 4:
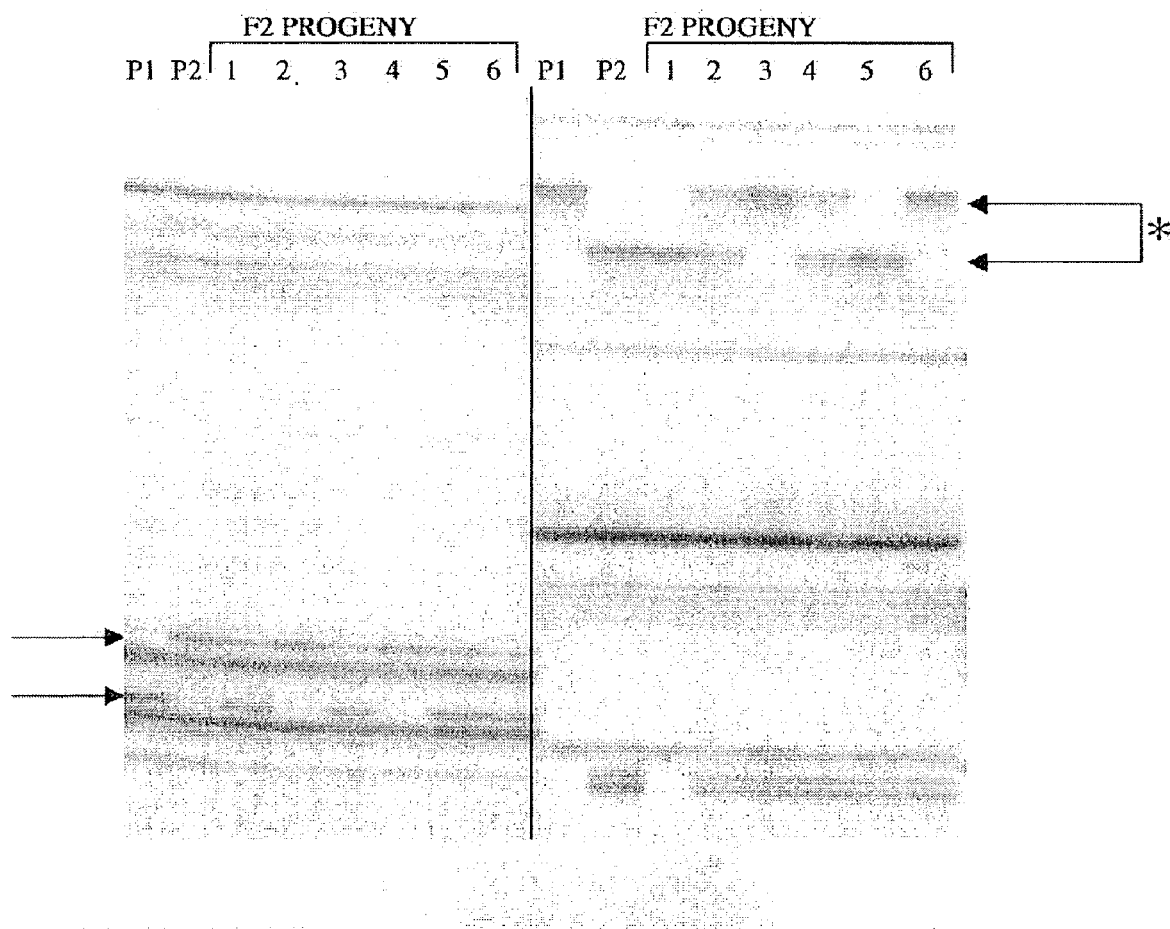
FIG. 4 shows a section in the 270–400 basepairs fragment mobility size range of the fingerprint patterns obtained from the parental lines and six F2 progeny of a pickle mapping population using the method of the invention, as further described in Example 2.

AFLP templates prepared using the restriction enzymes EcoRI and MseI and pre-amplification reactions were carried out as described in Example 1 or references incorporated therein. Microsatellite-repeat fragment-enriched fingerprints patterns were obtained by carrying out a selective amplification from 20-fold diluted +0/+0 pre-amplification mixture using the combination of an EcoRI AFLP selective +1 AFLP primer and a RAMP primer. The amplification reactions were carried out as described in Example 1. The results are shown in FIG. 4.

EcoRI+ 1 primers E01K (left hand side of FIG. 4) or E02K (right hand side of the FIG. 4) were used in combination with RAMP primer 98L33, which is directed at CA-repeat sequences. RAMP primer 98L33 was end-labelled with $^{33}$P. The amplification mixtures were resolved on an AFLP (sequence) gel, which was run, processed and exposed as described in Example 1.

The sequences of the adapters, AFLP pre-amplification primers and (selective AFLP) amplification primers used are as follows:

```
EcoRI adapter:
91M35:   5'-CTCGTAGACTGCGTACC-3'      (SEQ ID No.14)

91M36:   3'-CTGACGCATGGTTAA-5'        (SEQ ID No.15)

EcoRI+0 pre-amplification AFLP primer:
E00L:    5'-GTAGACTGCGTACCAATTC-3'    (SEQ ID No.16)

EcoRI AFLP primer sequences:
E01K:    5-GACTGCGTACCAATTCA-3'       (SEQ ID No.17)

E02K:    5-GACTGCGTACCAATTCC-3'       (SEQ ID No.18)
```

-continued

```
MseI adapter: (see example 1)
MseI + 0 pre-ampliflcation AFLP primer:
M00K     5'-GATGAGTCCTGAGTAA-3'     (SEQ ID No.19)

RAMP amplification primer:
98L33:   5'-CTCGATTTACACACAC-3'     (SEQ ID No.20)
```

3. Results

FIG. 4 shows a section in the 270–400 basepairs range of the fingerprint patterns obtained after separating the amplified fragments on a sequence gel. The fingerprints on the left-hand side of FIG. 4 were obtained with primer combination E01K/98L33 from pickle parental lines G421 (P1), H19 (P2) and six F2 offspring 001, 002, 003, 004, 005 and 006. The six F2s were loaded in lanes 1 through 6, respectively. The fingerprints on the right hand side of FIG. 4 were obtained with primer combination E02K/98L33 from the same pickle lines, applied to the gel in the same order.

The bands indicated by arrows may represent alleles of polymorphic microsatellite repeat loci, targeted by the RAMP primer used. FIG. 4 also demonstrates that different fingerprint patterns are obtained when the same RAMP primer is used in combination with a different selective AFLP primer, as would be expected from selective amplification with (an) AFLP primer(s).

4. Confirmation of Targeting a Microsatellite Repeat by Nucleotide Sequencing

The two bands at the top right hand part of FIG. 4, amplified using primer combination E02K/98L33 and indicated by arrows and a star (*) at the side, may represent two alleles of a microsatellite repeat locus. In order to demonstrate this, the nucleotide sequences of these fragments were determined after excision of the bands in G421 (P1) and H19 (P2) and re-amplification with the primers 98A28 and 98L33 according to the procedures described in Example 1.
98A28 (SEQ ID No.21):
5'-AGCGGATAACAATTTCACACAGGATA-
GACTGCGTACCAAT-3'

The two resulting sequences, truncated at the EcoRI site, are given in SEQ ID NOs. 22–23 and in FIG. 8, i.e:
SEQ ID No.22: 373 basepairs: "upper" band (G421)
SEQ ID No.23: 357 basepairs: "lower" band (H$_{19}$)

5. Conclusion

From FIG. 4 and inspection of the sequences of SEQ ID Nos 22 and 23 and FIG. 8 it is apparent that the length difference between these fragments results from a 10 basepairs insertion/deletion polymorphism located in the internal sequence of the fragment and a 6 basepair insertion/deletion polymorphism at the boundary of a GT microsatellite-repeat. This microsatellite-repeat is targeted at its opposite boundary by RAMP primer 98L33. Thus, it is very likely that these two sequences are allelic sequences derived from the same microsatellite-repeat locus.

Example 3

Targeting of Microsatellite Repeat Polymorphisms in Maize Using the Combination of an AFLP Primer and a RAMP Primer 1. Description of Biological Materials The biological materials used are the parental lines and 32 F2 progeny of maize mapping population. The parental lines are A7 (indicated by PI in FIG. 5) and B73 (indicated by P2 in FIG. 5). The F2 progeny used are numbered 001–032.

2. PstI/MseI AFLP Template Preparation, Pre-amplification and Amplification Using a Selective PstI Primer in Combination with a RAMP Primer.

AFLP templates prepared using the restriction enzymes PstI and MseI and pre-amplification reactions were carried out as described in Example 1 or references incorporated therein. Microsatellite-repeat fragment-enriched fingerprints patterns were obtained by carrying out a selective amplification from 20-fold diluted +0/+0 pre-amplification mixture using the combination of a PstI AFLP selective +2 AFLP primer and a RAMP primer. The amplification reactions were carried out as described in Example 1.

Figure 5:
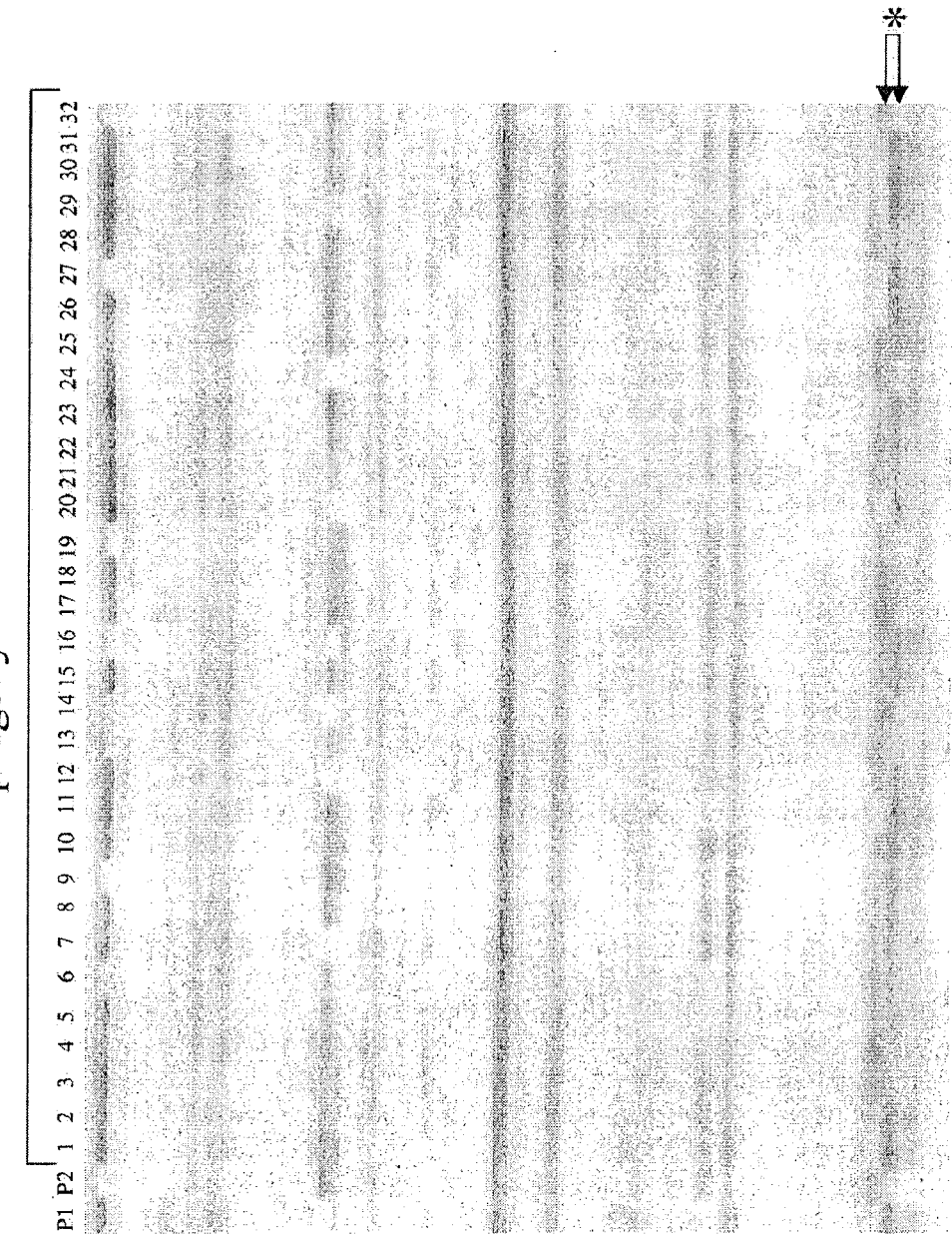
FIG. 5 shows a section in the 180–330 basepairs fragment mobility size range of the fingerprint patterns obtained from the parental lines and 32 F2 progeny of maize mapping population using the method of the invention, as further described in Example 3.

For the results shown in FIG. 5, PstI +2 primer P16 was used in combination with RAMP primer 98L39, which is directed at GA-repeat sequences. RAMP primer 98L39 was end-labelled with $^{33}$P. The amplification mixtures were resolved on an AFLP (sequence) gel, which was run, processed and exposed as described in Example 1.

The sequences of the adapters, AFLP pre-amplification primers and (selective AFLP) amplification primers used are as follows:

```
PstI adapter:
91D01: 5'-CTCGTAGACTGCGTACATGCA-3'     (SEQ ID No.24)

91D02  3'-CATCTGACGCATGT-5'            (SEQ ID No.25)

PstI+0 pre-amplification AFLP primer:
POOL:  5-GTAGACTGCGTACATGCAG-3'        (SEQ ID No.26)

PstI+2 selective amplification AFLP primer
P16:   5-GACTGCGTACATGCAGCC-3'         (SEQ ID No.27)

MseI adapter: (see example 1)
MseI+0 pre-amplification AFLP primer:
M00K (see example 2)
RAMP amplification primer:
98L39: 5'-GATAAGCGGAGAGAGA-3'          (SEQ ID No.28)
```

3. Results

FIG. 5 shows a section in the 180–330 basepairs range of the fingerprint patterns obtained after separating the amplified fragments on a sequence gel. The parental lines B73 (P1) and A7(P2) and 32 F2 progeny as described in section 1 were loaded in the lanes indicated by P1, P2 and the numbers 1 through 32, respectively. The bands indicated by arrows may represent alleles of a polymorphic microsatellite repeat locus, targeted by the RAMP primer used.

4. Confirmation of Targeting a Microsatellite Repeat by Nucleotide Sequencing

The two bands at the bottom part of FIG. 5, amplified using primer combination P16/98L39 and indicated by arrows and a star (*) at the side, may represent two alleles of a microsatellite repeat locus. In order to demonstrate this, the nucleotide sequences of these fragments were determined after excision of the bands in B73 (P1) and A7 (P2) and re-amplification with the primers 98L39 and 98L89 according to the procedures described in Example 1.
98L89 (SEQ ID No.29):
5'-AGCGATAACAATTTCACACAGGATA-
GACTGCGTACCTGC-3'

The two resulting sequences, truncated at the PstI site, are given in SEQ ID NOs 30–31 and FIG. 8, i.e.:
SEQ ID No.30: 170 basepairs: "upper" band (A7)
SEQ ID No.31: 168 basepairs: "lower" band (B73)

5. Conclusion

From FIG. 5 and inspection of the sequences of SEQ IDs NOs 30–31 and FIG. 8, it is apparent that the length difference between these fragments results from a 2 basepairs insertion/deletion polymorphism located at the boundary of a CT (GA) microsatellite-repeat. This microsatelliterepeat is targeted by RAMP primer 98L39. In addition, there are nine base substitutions distinguishing the two sequences. Thus, it is very likely that these two sequences are allelic sequences derived from the same microsatellite-repeat locus.

Example 4

Targeting of Microsatellite Repeat Polymorphisms in Pepper Using the Combination of an AFLP Primer and a RAMP Primer 1. Description of Biological Materials The biological materials used are the parental lines and 26 F2 progeny of pepper mapping population. The parental lines are Maor (indicated by P1 in FIG. 6) and Perennial (indicated by P2 in FIG. 6). The F2 progeny used are numbered 019–030, 032–034, 036–041, and 043–047.

2. EcoRI/MseI AFLP Template Preparation Pre-amplification and Amplification Using a Selective EcoRI Primer in Combination with a RAMP Primer.

AFLP templates prepared using the restriction enzymes EcoRI and MseI and pre-amplification reactions were carried out as described in Example 1 or references incorporated therein. Microsatellite-repeat fragment-enriched fingerprints patterns were obtained by carrying out a selective amplification from 20-fold diluted +0/+0 pre-amplification mixture using the combination of an EcoRI AFLP selective +2 AFLP primer and a RAMP primer. The amplification reactions were carried out as described in Example 1. For the results shown in FIG. 6, EcoRI +2 primers E15 was used in combination with RAMP primer 99A52, which is directed at CA-repeat sequences. RAMP primer 99A52 was end-labelled with $^{33}$P. The amplification mixtures were resolved on an AFLP (sequence) gel, which was run, processed and exposed as described in Example 1.

The sequences of the adapters, AFLP pre-amplification primers and (selective AFLP) amplification primers used are as follows:

```
EcoRI adapter: (see example 1)
EcoRI AFLP + 0 pre-amplification primer: (see
example 1)
EcoRI AFLP + 2 selective amplification primer:
E15:    5'-GACTGCGTACCAATTCCA-3'    (SEQ ID No.32)

MseI adapter: (see example 1)
MseI AFLP + 0 pre-amplification primer:
M00K (see example 2)
RAMP amplification primer:
99A52:  5'-GATAAGCGCACACACA-3'    (SEQ ID No.33)
```

3. Results

Figure 6:
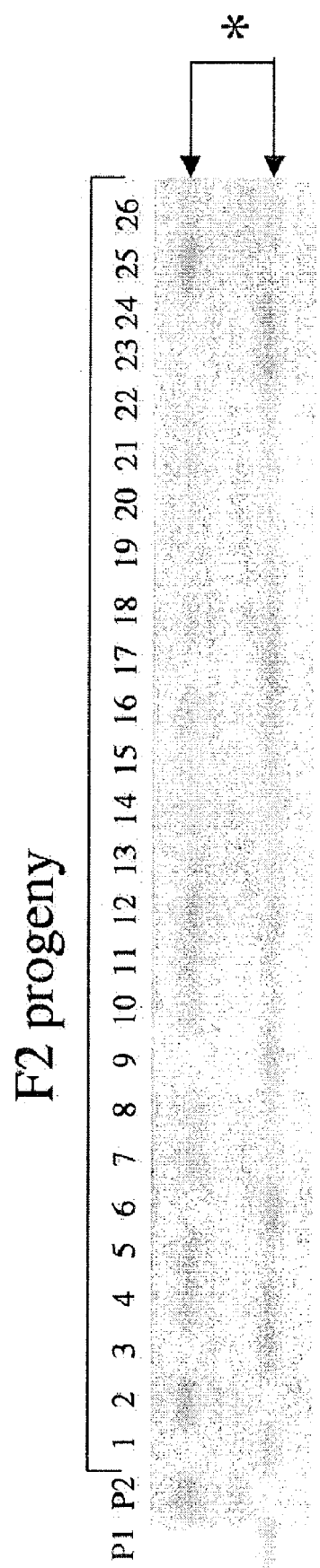
FIG. 6 shows a section in the 105–110 basepairs fragment mobility size range of the fingerprint patterns obtained from the parental lines and 26 F2 progeny of pepper mapping population using the method of the invention, as further described in Example 4.

FIG. 6 shows a section in the 105–110 basepairs range of the fingerprint patterns, obtained after separating the amplified fragments on a sequence gel. The parental lines Maor (P1), Perennial (P2) and 26 F2 progeny as described in section 1 were loaded in the lanes indicated by P1, P2 and the numbers 1 through 26, respectively. The bands indicated by arrows may represent alleles of a polymorphic microsatellite repeat locus, targeted by RAMP primer 99A52.

4. Confirmation of Targeting Microsatellite Repeats by Nucleotide Sequencing

The two strong bands shown in FIG. 6, which are indicated by arrows and a star (*) at the side, may represent two alleles of a microsatellite repeat locus. In order to demonstrate this, the nucleotide sequences of these fragments were determined after excision of the bands in Perennial (P2) and Maor (P2) and re-amplification with the primers 98A28 (see Example 2) and 99A52 according to the procedures described in Example 1.

The two resulting sequences, truncated at the EcoRI site, are given in SEQ ID Nos 34–35 and in FIG. 8, i.e.:
SEQ ID No.34: 98 basepairs: "upper" band (Perennial)
SEQ ID No.35: 95 basepairs: "lower" band (Maor)

5. Conclusion

From FIG. 6 and inspection of the sequences of SEQ ID Nos. 34 and 35 and FIG. 8, it is apparent that the length difference between these fragments results from a 3 basepairs insertion/deletion polymorphism located at the boundary of a GT (CA) microsatellite-repeat. This microsatelliterepeat is targeted by RAMP primer 99A52. In addition, there is a one base substitution in the internal sequence of the fragment distinguishing the two sequences. Thus, it is very likely that these two sequences are allelic sequences derived from the same microsatellite-repeat locus.

Example 5

Partial Complementarity of Fingerprint Patterns Generated Using an AFLP Primer in Combination with RAMP Primers Containing Different Anchor Sequences at the 5'-prime End but Identical Dinucleotide Repeat Motifs 1. Description of Biological Materials The biological materials used are the parental lines and 6 F2 progeny of a maize mapping population. The parental lines are B73 (indicated by P1 in FIG. 7) and A7 (indicated by P2 in FIG. 7). The F2 progeny are numbered 021, 024, 025, 026, 027, and 031.

2. PstI/MseI Template Preparation and Amplification Using a Selective AFLP Primer in Combination with RAMP Primers with Identical Repeat Sequences but Different 5'-Anchor Sequences.

AFLP templates prepared using the restriction enzymes PstI and MseI and pre-amplification reactions were carried out as described in Example 1 or references incorporated therein. Microsatellite-repeat fragment-enriched fingerprints patterns were obtained by carrying out a selective amplification from 20-fold diluted +0/+0 pre-amplification mixture using the combination of a PstI AFLP selective +2 primer and a RAMP primer. The amplification reactions were carried out as described in Example 1. For the results shown in FIG. 7, three RAMP primers with different 5 prime "anchor" sequences but identical dinucleotide repeat sequences were used. These RAMP primers are named 98L36, 98L37 and 98L76 and are directed a CT-repeat sequences. The amplification conditions used were as described in Example 1 or references incorporated therein. For the fingerprint patterns shown in FIG. 7, the P17 primer was end-labelled with $^{33}$P and the amplification mixtures were resolved on a standard AFLP (sequence) gel, which was run, processes and exposed as described in Example 1.

The sequences of the adapters, AFLP- and RAMP primers used are as follows:

```
PstI + 0 pre-amplification AFLP primer:
(see example 3)
PstI + 2 selective amplification AFLP primer
P17:      5-GACTGCGTACATGCAGCG-3'    (SEQ ID No.36)

MseI adapter: (see example 1)
MseI + 0 pre-amplification AFLP primer:
M00K (see example 2)
RAMP amplification primer:
98L36:    5'-CAGCTAAGCTCTCTCT-3'     (SEQ ID No.37)

98L37:    5'-CAGCATGACTCTCTCT-3'     (SEQ ID No.38)

98L76:    5'-GATAAGCGCTCTCTCT-3'     (SEQ ID No.39)
```

3. Results

Figure 7:
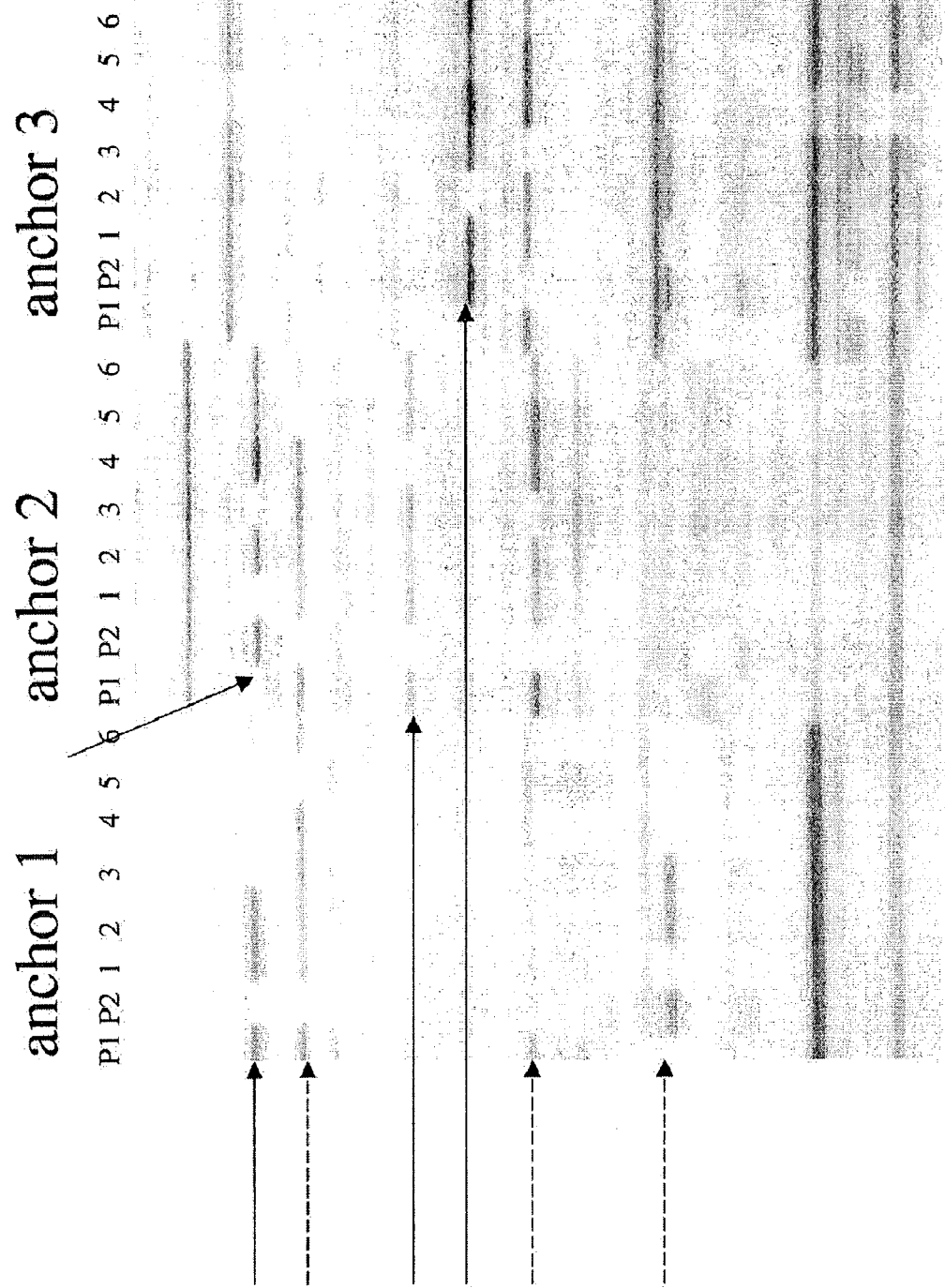
FIG. 7 shows a section in the 250–500 basepairs fragment mobility size range of the fingerprint patterns obtained from the parental lines and 6 F2 progeny of a maize mapping population using the method of the invention, as further described in Example 5.

FIG. 7 shows a section in the 250–500 basepairs range of the fingerprint patterns obtained after separating the amplified fragments on a sequence gel. The fingerprint patterns obtained with three primer combinations are shown for the parental lines B73 (P1) and A7 (P2) and six F2 progeny (indicated by the lane number 1 through 6). The RAMP primers used differ only at the 5 prime anchor sequences and are 98L36 (indicated by anchor 1), 98L37 (indicated by anchor 2) and 98L76 (indicated by anchor 3).

Fragments pointed at by arrows connected to a solid line represent bands that are amplified by only one of the three RAMP primers, whereas fragments pointed at by arrows connected to a dashed line are amplified by more than one AFLP-RAMP primer combination.

4. Conclusion

FIG. 7 shows that partially complementary fingerprint patterns are obtained when RAMP primers with different 5 prime anchor sequences but with identical microsatellite repeat sequences are used in combination with the same AFLP primer. This result suggests that amplification using RAMP primers with different anchor sequences is useful to maximise the number of targeted microsatellites.

FIG. 7 further shows that amplification of fragments from AFLP pre-amplification reactions using the combination of an AFLP primer and a RAMP primer is based in part on miss-priming between the RAMP anchor sequence on target sequences present in the AFLP pre-amplification mixture. With respect to the targeting S of microsatellite repeats polymorphisms this does not have an adverse effect, as long as correct anchoring at the boundary of the repeats take place, as shown in Examples 1–4.

Example 6

Figure 9:
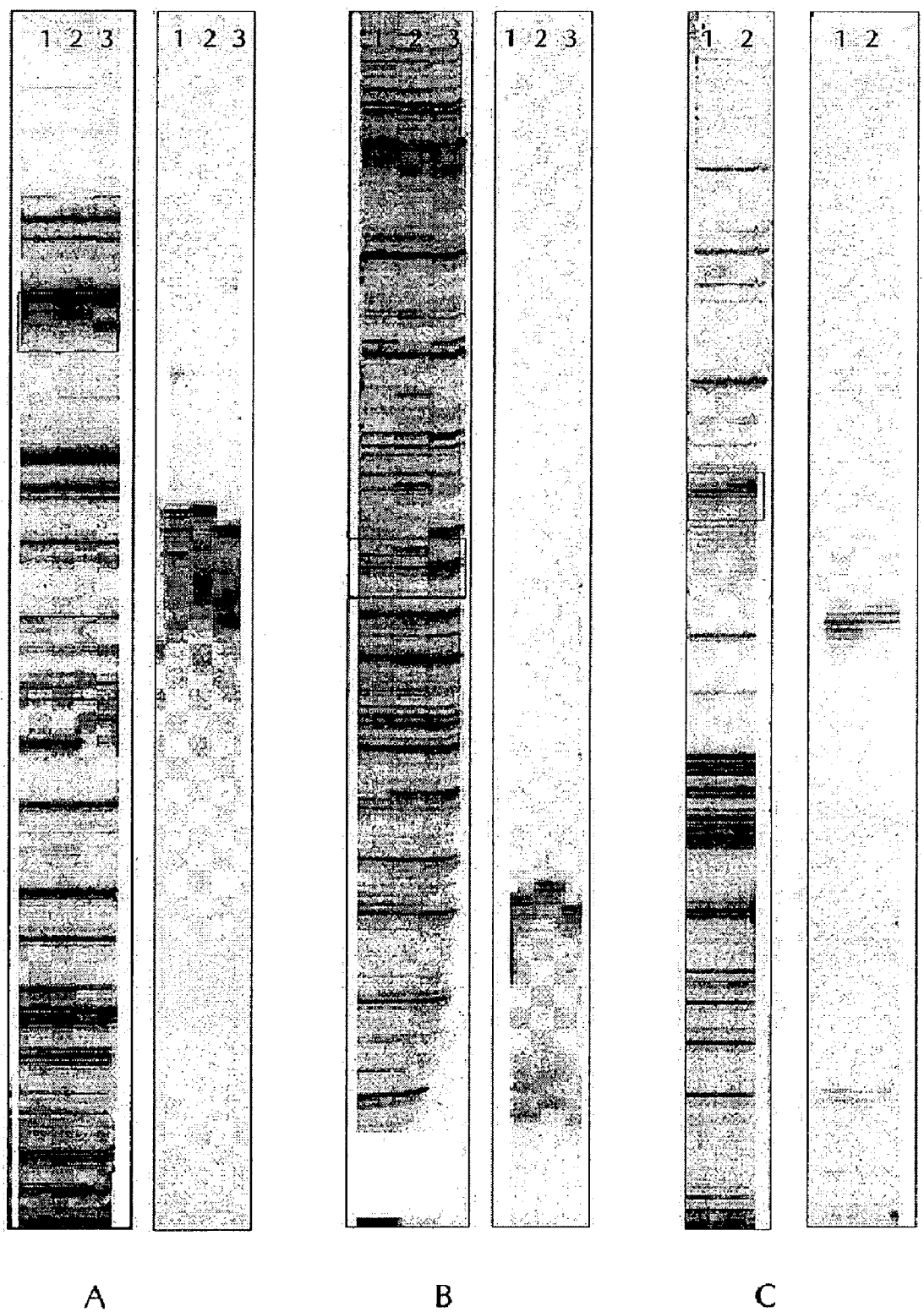
FIG. 9 shows conversion of polymorphic microsatellites to conventional PCR-assays.

Conversion of Microsatellite-AFLP®
(RAMP-AFLP®) Microsatellite to a Classical PCR
Assay Based on the Use of Flanking PCR Primers 1. Description of Biological Materials The materials used in this experiment are three lines of tomato (sample numbers 113, 132 and 205; FIG. 9 panel A, lanes 1, 2 and 3, respectively) and three lines of barley (sample numbers 42, 58 and 64; FIG. 9 panel B, lanes 1, 2 and 3, respectively). Lanes 1 and 2 in panel C of FIG. 9 represent tomato lines 113 and 132, respectively, which are identical to those in panel A.

2. Materials and Methods 2.1. Preparation of AFLP® Templates and Pre-Amplification Reactions AFLP® templates were prepared from genomic DNA of the three tomato and three barley samples described in section 1, using the restriction enzymes EcoRI (rare cutter) and MseI (frequent cutter), according to the conventional AFLP®-techniques and protocols, as described in EP-534858. Pre-amplification reactions were also carried out according to the EP-534858.

The sequences of the adapters, AFLP® pre-amplification primers and (selective AFLP®) amplification primers are as follows

```
EcoRI adapter:
91M35:    5'-CTCGTAGACTGCGTACC-3'    (SEQ ID No. 14)

91M36:    3'CATCTGACGCATGGTTAA-5'    (SEQ ID No. 40)

EcoRI+0 pre-amplification AFLP® primer:
E00L:     5-GTAGACTGCGTACCAATTC-3    (SEQ ID No. 16)

MseI adapter:
92A18:    5-GACGATGAGTCCTGAG-3       (SEQ ID No.1)

92A19:    5'-TACTCAGGACTCAT-3'       (SEQ ID No.2)

MseI+0 pre-amplification primer:
93E40     5-GATGAGTCCTGAGTAA-3  (SEQ
(M00K):   ID No. 19)

MseI+1 selective amplification primer:
93E44:    5-GATGAGTCCTGAGTAAT-3      (SEQ ID No. 41)
```

2.2. Generation of RAMP Microsatellite Containing Fingerprints

Figure 1:
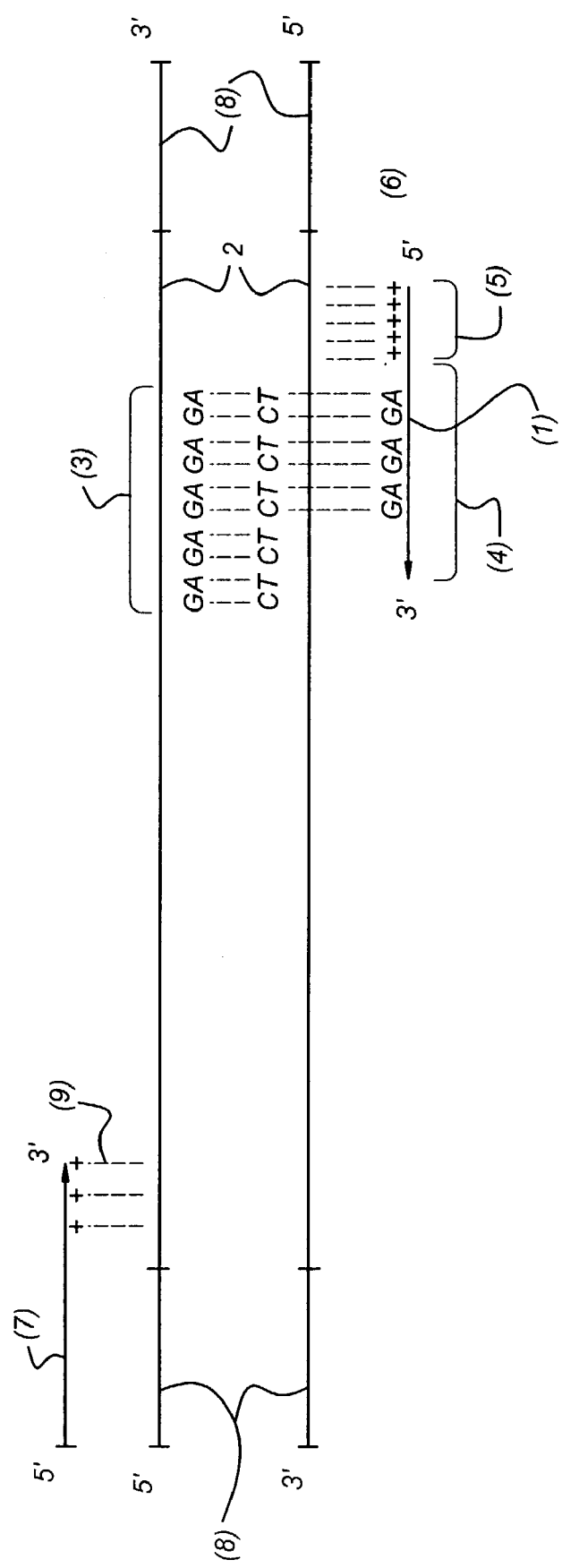

Microsatellite AFLP® fingerprints as depicted on the left side of panels A, B and C in FIG. 1 were generated according to the procedures as described hereinbefore.

For the three tomato lines depicted in panel A in FIG. 9, the sequences of the combination of selective AFLP® +2 primer E25 and RAMP primer 99A54 were:

```
E25 (93C47):  5-GACTGCGTACCAATTCTG-3  (SEQ ID No.42)

99A54:        5'-GACGGCACGAGAGAGA-3'  (SEQ ID No.9)
``` of which RAMP primer 99A54 is directed at targeting GA dinucleotide repeat motifs.

For the three barley depicted in panel B in FIG. 9, the sequences of the combination of selective AFLP® +2 primer E22 and RAMP primer 98L38 were:

```
E22 (93C44):  5-GACTGCGTACCAATTCGT-3  (SEQ ID No.43)

98L38:        5'-GATAGCACGAGAGAGA-3'  (SEQ ID No.44)
``` of which RAMP primer 98L38 is directed at targeting GA dinucleotide repeat motifs.

For the two tomato lines depicted in panel C in FIG. 9, the sequences of the combination of selective AFLP® +2 primer E16 (93C38) and RAMP primer 99A58 were:

```
E16 (93C38):  5-GACTGCGTACCAATTCCC-3  (SEQ ID No.45)

99A58:        5'-GACTGTACCACACACA-3   (SEQ ID No.46)
``` of which RAMP primer 99A58 is directed at targeting CA dinucleotide repeat motifs.

2.3. Conversion of Microsatellites Identified in Microsatellite-AFLP® Fingerprints The microsatellites of tomato and barley identified in the microsatellite-AFLP®-fingerprints shown on the left-hand side of panels A and B in FIG. 9, were converted to a PCR assay with two locus-specific flanking PCR primers according to the method described hereinbefore.

The microsatellite of tomato identified in the microsatellite-AFLP® fingerprints shown on the left-hand side of panel C in FIG. 9, was converted to a PCR assay with one locus-specific PCR primer and a selective AFLP®+2 MseI primer, according to the method described hereinbefore.

2.3.1. Re-Amplification and Sequence Determination of Microsatellite-containing Fragment Present in the Microsatellite-AFLP® Fingerprint, Including Selection of PCR Primer 1.

First, the bands representing the microsatellite alleles were excised from the sequence gel and re-amplified by PCR with the combination of an EcoRI-AFLP® primer with M13 sequence and a RAMP primer that was originally used to generate the microsatellite-AFLP® fingerprint pattern in which the microsatellite polymorphism was observed. In case of the three tomato lines depicted in panel A of FIG. 9 these primers were 99A54/98A28, in case of the three barley lines in panel B these primers were 98L38/98A28, and in case of the two tomato lines in panel C these primers were 99A58/98A28 Primer 99A28 contains an M13 sequence at its 5' end:

98A28:    5'-AGCGATAACAATTTCACACAGGATA-
    GACTGCGTACCAAT-3' (SEQ ID NO. 21)

Note: the M13 sequence at the 5' end of 98A28 allows priming in the subsequent sequence reaction with a universal M13 sequence primer).

Next, the sequences of the PCR products representing the microsatellites alleles were determined by dideoxy sequencing using fluorescently labelled ddNTPs, according to standard procedures. From the sequences thus obtained, the first flanking PCR primer was designed (PCR primer 1). The sequences of PCR primers 1 for the microsatellites in panels A, B and C are, respectively:

```
00N42: 5'-TAGTATCTGAAGCTCGGAGG-3'    (SEQ ID No.47)

00N45: 5'-CGGACGAAGTTCCCTAGCAC-3'    (SEQ ID No.48)

00R66: 5'-CAACTTGAGTTACATTTGTGC-3'   (SEQ ID No.49)
```

2.3.2. PCR Amplification of the RAMP-MseI Fragment in Order to Obtain the Second Flanking Sequence, and Validation on Genomic DNA or AFLP® Pre-amplification Reaction.

With the sequence of the EcoRI-RAMP fragment available, only the sequence of the RAMP-MseI part of the EcoRI/MseI restriction fragment harbouring the microsatellite repeat sequence targeted by the RAMP primer is missing in order to design the second flanking PCR primer (PCR primer 2). These RAMP-MseI fragments were amplified, and the remainder of the conversion process were carried out, as follows:

Microsatellite of Tomato in Panel A of FIG. 9:

Standard EcoRI/MseI pre-amplification reactions carried out using +0/+0 AFLP® amplification primers (sequences as described above), were taken as the starting material. Next a further selective AFLP® amplification was carried out using all of the four MseI+1 primers in combination with PCR primer OON42 (the sequence of one of these MseI+1 primers is shown above, and the other three differ from this sequence only at the most 3' primed base). The PCR profile used was that of a regular AFLP® pre-amplification reaction and described in EP-534858.

The reaction products were resolved on a standard sequence gel and the results of the amplifications with the four different MseI+1 primers compared in order to determined the likely +1 base at the MseI side of the fragment of interest (This determination was based on recognition of the known length differences between the microsatellite-AFLP® alleles in one of the four PCR reactions).

Next, the sequence of the Primer 1-MseI+1 fragment was determined using standard dideoxy sequencing after excision of the fragment from the gel and re-amplification by PCR using primer 00N42, and primer 99G24 which contains an M13 sequence at its 5' end:

99G24: (SEQ ID No. 50)
5'-CGGGAGGGTTTTCCCAGTCACGACAC-
    GACTCACTGATGAGTCCTGAGTAA-3'

Note: the M13 sequence at the 5' end of 99G24 allows priming in the subsequent sequence reaction with a universal M13 sequence primer).

Next, PCR primer 2 (00R73) was selected from the sequence obtained above. PCR primer 2 is always chosen from the complementary strand of PCR primer 1 (00N42), in order to allow PCR amplification of the microsatellite-containing fragment. The sequence of 00R73 is:

00R73:  5'-GTTGGATCCACTCTTCTGATC-3; (SEQ ID No. 51)

Finally, validation of the ability of the selected primers 00N42 and 00R73 to selectively amplify the region of the tomato genome containing the microsatellite identified by microsatellite-AFLP® was conducted by carrying out a PCR reaction starting with about 50 ng genomic DNA of tomato lines 113, 132 and 205, primers 00N42 and 00N73 and amplifying conditions according to the following PCR profile (AFLP® pre-amplification profile): 3 minutes at 94° C., followed by 30 cycles of 30 seconds at 94° C., 1 minute at 55° C., 1 minute at 72° C.), and resolving the PCR products on a standard sequence (AFLP®) gel.

The results are shown on the right side of panel A in FIG. 9, which indicates that using primers 00N42 and 00R73, the desired microsatellite is amplified specifically, as judged the length differences between the PCR products obtained from tomato lines 113, 132 and 205, which match the length differences observed in the corresponding microsatellite-AFLP® fingerprints shown on the left hand side of panel A in FIG. 9.

Microsatellite of Barley in Panel B of FIG. 9:

Conversion and validation of the microsatellite of barley in panel B of FIG. 9 was carried out as described above for the microsatellite of tomato, with the exception that the sequence of PCR primer 1 was 00N45 (sequence above) and the sequence of PCR primer 2 was 00R74:

00R74: 5'-GCGTTGAGCAGGCATTCGGA-3' (SEQ ID No. 52)

and EcoRI/MseI +0/+0 AFLP® pre-amplification reactions and genomic DNA of the barley samples 42, 58 and 64 were taken as the starting materials for conversion and validation, respectively. The PCR products resulting from amplification from genomic DNA (validation) with primers 00N45 and 00R74 are shown on the right hand side in panel B of FIG. 9.

Microsatellite of Tomato in Panel C of FIG. 9:

Conversion and validation of the microsatellite of tomato in panel C of FIG. 9 was carried out as described above for the microsatellite of tomato in panel A, with the following exceptions: the sequence of PCR primer 1 was 00R66

(sequence above) and the sequence of PCR primer 2 was AFLP® +2 selective amplification primers M23:
M23: 5'-GATGAGTCCTGAGTAATC-3 (SEQ ID No. 53)

The reason for using an Mse+2 AFLP® primer instead of a locus specific (conventional) PCR primer (PCR primer 2) was that sequence analysis of the 00R66-MseI fragment revealed that the microsatellite was located very close to the MseI adapter sequence, which prevented the design of a specific primer 2. Consequently, amplification of the microsatellite from genomic DNA can not be carried out because the sequence of M23 is not present in the tomato genome. Hence, in order to achieve specific amplification of only this microsatellite (conversion) in a PCR assay, EcoRI/MseI+0/+1 pre-amplification reactions were taken from tomato samples 113 and 132) and used as the starting materials to amplify the microsatellite using primers 00R66 and M23 according to the AFLP® selective amplification profile (described in EP-534858). The resulting PCR products are shown on the right-hand side in panel C of FIG. 9. As for the other two examples, conversion of this microsatellite to a PCR assay is demonstrated, as judged by the length differences of the PCR products, which match those in the microsatellite-AFLP® fingerprints of the same samples.

The problem with a too small distance between the microsatellite and the MseI restriction site and the associated problem of designing the second PCR-primer can be resolved, for example in the present case of the above described EcoRI/MseI restriction fragment by carrying out an additional procedure using the EcoRI restriction enzyme combined with an other frequent cutter restriction enzyme and matching adapters. Important is, that this new frequent cutter does not cut in the known sequence between the RAMP primer en the EcoRI AFLP® primer.

The first PCR primer combined with an AFLP® primer of the new frequent cutter is subsequently used to identify the restriction fragment containing the microsatellite of interest. The sequence of this restriction fragment can be determined beyond (i.e. downstream of the microsatellite) using a sequencing primer from the frequent cutter restriction site towards the microsatellite. Doing so, a sequence has been revealed which does have a sufficient length for designing a suitable PCR-primer for use as the second PCR-primer in the SRR-assay.

The invention claimed is:

1. Method for analysing a nucleic acid sequence, the method at least comprising the steps of:
  (a) amplifying a restriction fragment generated from the nucleic acid to be analysed, in which the restriction fragment has been ligated to an adapter, and whereby a RAMP-primer and an AFLP-primer are used to amplify the nucleic acid sequence; wherein said RAMP primer comprises a 3'-part complementary to a compound microsatellite repeat and a 5'-part complementary to the nucleotides directly adjacent to the compound microsatellite repeat, said 5'-part consisting of 4–10 non-degenerate nucleotides; and wherein said AFLP primer is complementary to said adapter and optionally contains at its 3' end between 1 and 6 selective nucleotides;

and optionally comprising the further step of:
  (b) detecting the amplified nucleic acid sequences thus obtained.

2. Method for analysing a nucleic acid sequence, the method comprising the steps of:
  (a) restricting the starting nucleic acid with a restriction endonuclease to provide a mixture of restriction fragments;
  (b) ligating the restriction fragments thus obtained to an adapter;
  (c) amplifying the mixture of adapter-ligated restriction fragments thus obtained with a RAMP-primer and an AFLP-primer to provide a mixture of amplified restriction fragments; wherein said RAMP primer comprises a 3'-part complementary to a compound microsatellite repeat and a 5'-part complementary to the nucleotides directly adjacent to the compound microsatellite repeat, said 5'-part consisting of 4–10 non-degenerate nucleotides; and wherein said AFLP primer is complementary to said adapter and optionally contains at its 3' end between 1 and 6 selective nucleotides;

and optionally comprising the further step of:
  (d) detecting the amplified restriction fragments thus obtained.

3. Method according to claim 1 or 2, in which the starting nucleic acid is a nucleic acid that contains or is suspected to contain a compound microsatellite.

4. Method for providing a PCR primer or a pair of PCR primers for use in the amplification of a PCR fragment spanning a compound microsatellite-associated genomic polymorphism, the method comprising the steps of:
  a) identification of a fragment containing the compound microsatellite-associated genomic polymorphism, whereby the fragment is amplified by the combined use of a RAMP primer and a first AFLP primer; wherein said RAMP primer comprises a 3'-part complementary to a compound microsatellite repeat and a 5'-part complementary to the nucleotides directly adjacent to the compound microsatellite repeat, said 5'-part consisting of 4–10 non-degenerate nucleotides; and wherein said AFLP primer is complementary to a first adapter and optionally contains at its 3' end between 1 and 6 selective nucleotides;
  b) sequencing the polymorphic fragment;
  c) synthesising a first PCR-primer corresponding to a sequence flanking the compound microsatellite repeat sequence at the 3' end;
  d) optionally, amplifying a fragment comprising the compound microsatellite-associated genomic polymorphism and sequences flanking the microsatellite-associated genomic polymorphism at its 5'-end, using the first PCR-primer and a second AFLP primer, said second AFLP primer being complementary to a second adapter and optionally contains at its 3' end between 1 and 6 selective nucleotides; and, optionally, synthesising a second PCR-primer corresponding to a sequence flanking the compound microsatellite repeat sequence at the 5' end.

5. Method for providing a PCR-primer, comprising the steps of:
  a) restricting a nucleic acid sequence with at least one restriction endonuclease to provide a mixture of restriction fragments;
  b) ligating the restriction fragments thus obtained to at least one adapter;
  c) amplifying the mixture of adapter ligated restriction fragments thus obtained with at least one RAMP-primer and at least one first AFLP primer to provide a mixture of amplified restriction fragments; wherein said RAMP primer comprises a 3'-part complementary to a compound microsatellite repeat and a 5'-part complementary to the nucleotides directly adjacent to the compound microsatellite repeat, said 5'-part consisting of 4–10 non-degenerate nucleotides; and wherein said AFLP primer is complementary to said adapter and optionally contains at its 3' end between 1 and 6 selective nucleotides;

d) detecting at least one of the amplified restriction fragments thus obtained;

e) identifying at least one compound microsatellite-associated polymorphic fragment;

f) determining the sequence of said polymorphic fragment;

g) synthesising a first PCR-primer corresponding to a sequence flanking the compound microsatellite repeat sequence at the 3' end;

h) optionally, amplifying a fragment comprising the compound microsatellite and at least part of the 5'-flanking sequence using the first PCR-primer and a second AFLP primer; and i) optionally, synthesising a first PCR-primer corresponding to a sequence flanking the compound microsatellite repeat sequence at the 5' end.

6. Method according to claim 1, 2, 4 or 5, in which the starting nucleic acid comprises a eukaryotic genomic DNA or cDNA or a mixture or a library of recombinant DNA clones derived from a plant, animal or a human.

7. Method according to claim 1, 2, 4 or 5, in which the starting nucleic acid is derived from wheat, barley, maize, tomato, pepper, lettuce, rice or soybean; from animals; or from a human being.

8. Method according to claim 1, 2, 4 or 5 in which the nucleotides of the RAMP primer that form the 5'-part complementary to the nucleotides directly adjacent to the compound microsatellite repeat are arbitrary non-degenerate nucleotides.

9. Method according to claim 1, 2, 4 or 5 in which the RAMP primer contains a total of between 8 and 20 nucleotides.

10. Method according to claim 1, 2, 4 or 5 in which, of the nucleotides present in the RAMP primer, between 6 to 8 nucleotides are complementary to a compound repeat motif of a microsatellite, and the remainder of the nucleotides present in the RAMP-primer form the 5'-part complementary to the nucleotides directly adjacent to the compound microsatellite repeat.

11. Kit comprising a RAMP primer and an AFLP primer, wherein said RAMP primer comprises a 3'-part complementary to a compound microsatellite repeat and a 5'-part complementary to the nucleotides directly adjacent to the compound microsatellite repeat, said 5'-part consisting of 4–10 non-degenerate nucleotides; and wherein said AFLP primer is complementary to an adapter and optionally contains at its 3' end between 1 and 6 selective nucleotides.

12. Kit comprising PCR-primers obtained by the method of claim 4 or 5.

13. Method according to claim 1, 2, 4 or 5, in which two adapter sequences have been ligated to the restriction fragment.

14. Method according to claim 1, 2, 4 or 5, in which, of the nucleotides present in the RAMP-primer, 4 to 10 nucleotides are complementary to a repeat motif of a compound microsatellite and 6 to 8 nucleotides are complementary to the nucleotides directly adjacent to the compound microsatellite repeat.

15. Method according to claim 14, in which said 6 to 8 nucleotides complementary to the nucleotides directly adjacent to the compound microsatellite repeat are non-degenerate nucleotides.

16. Method according to claim 14, in which said 6 to 8 nucleotides complementary to the nucleotides directly adjacent to the compound microsatellite repeat are non-degenerate, arbitrary nucleotides.

17. The kit according to claim 11, further comprising at least one adapter and optionally restriction enzymes.

* * * * *

SEQUENCE LISTING

```
<160> NUMBER OF SEQ ID NOS: 53

<210> SEQ ID NO 1
<211> LENGTH: 16
<212> TYPE: DNA
<213> ORGANISM: Artificial
<220> FEATURE:
<223> OTHER INFORMATION: adapter

<400> SEQUENCE: 1
gacgatgagt cctgag                                                    16

<210> SEQ ID NO 2
<211> LENGTH: 14
<212> TYPE: DNA
<213> ORGANISM: Artificial
<220> FEATURE:
<223> OTHER INFORMATION: adapter

<400> SEQUENCE: 2
tactcaggac tcat                                                      14

<210> SEQ ID NO 3
<211> LENGTH: 19
<212> TYPE: DNA
<213> ORGANISM: Artificial
<220> FEATURE:
<223> OTHER INFORMATION: pre-amplification primer

<400> SEQUENCE: 3
gacgatgagt cctgagtaa                                                 19

<210> SEQ ID NO 4
<211> LENGTH: 16
<212> TYPE: DNA
<213> ORGANISM: Artificial
<220> FEATURE:
<223> OTHER INFORMATION: adapter
```

```
<400> SEQUENCE: 4
ctcgtagact gagtac                                                    16

<210> SEQ ID NO 5
<211> LENGTH: 13
<212> TYPE: DNA
<213> ORGANISM: Artificial
<220> FEATURE:
<223> OTHER INFORMATION: adapter

<400> SEQUENCE: 5
cggtacgcag tct                                                       13

<210> SEQ ID NO 6
<211> LENGTH: 16
<212> TYPE: DNA
<213> ORGANISM: Artificial
<220> FEATURE:
<223> OTHER INFORMATION: pre-amplification primer

<400> SEQUENCE: 6
gtagactgcg taccga                                                    16

<210> SEQ ID NO 7
<211> LENGTH: 19
<212> TYPE: DNA
<213> ORGANISM: Artificial
<220> FEATURE:
<223> OTHER INFORMATION: AFLP primer

<400> SEQUENCE: 7
gtagactgcg taccgacac                                                 19

<210> SEQ ID NO 8
<211> LENGTH: 16
<212> TYPE: DNA
<213> ORGANISM: Artificial
<220> FEATURE:
<223> OTHER INFORMATION: RAMP primer

<400> SEQUENCE: 8
gataagcgct ctctct                                                    16

<210> SEQ ID NO 9
<211> LENGTH: 16
<212> TYPE: DNA
<213> ORGANISM: Artificial
<220> FEATURE:
<223> OTHER INFORMATION: RAMP primer

<400> SEQUENCE: 9
gacggcacga gagaga                                                    16

<210> SEQ ID NO 10
<211> LENGTH: 49
<212> TYPE: DNA
<213> ORGANISM: Artificial
<220> FEATURE:
<223> OTHER INFORMATION: primer

<400> SEQUENCE: 10
agcggataac aatttcacac aggacacact ggtatagact gcgtaccga                49

<210> SEQ ID NO 11
<211> LENGTH: 260
```

-continued

```
<212> TYPE: DNA
<213> ORGANISM: lettuce
<220> FEATURE:
<221> NAME/KEY: misc_feature
<222> LOCATION: (117)..(117)
<223> OTHER INFORMATION: n is a, c, g, or t

<400> SEQUENCE: 11
tcgacacaaa atccgaggct gtcaggcccc ccacgacgtg gtgaagaagc cacgacgtgg      60
tattgtgatt gatgggtgcc aggtgcgtca cgaaacgtct cgtcaacaga agaggantag    120
aatccctcac cacgacgtgg tgacatggcg cccaaattag ggctataaat agcagccgaa    180
ggtgttgggt tccattgctt atttcttctc tctctctctc tctctctctc tctctctctc    240
tctctctctc tcgtgccgtc                                                260

<210> SEQ ID NO 12
<211> LENGTH: 256
<212> TYPE: DNA
<213> ORGANISM: lettuce
<220> FEATURE:
<221> NAME/KEY: misc_feature
<222> LOCATION: (117)..(117)
<223> OTHER INFORMATION: n is a, c, g, or t

<400> SEQUENCE: 12
tcgacacaaa atccgaggct gtcaggcccc ccacgacgtg gtgaagaagc cacgacgtgg      60
tattgtgatt gatgggtgcc aggtgcgtca cgaaacgtct cgtcaacaga agaggantag    120
aatccctcac cacgacgtgg tgacatggcg cccaaattag ggctataaat agcagccgaa    180
ggtgttgggt tccattgctt atttcttctc tctctctctc tctctctctc tctctctctc    240
tctctctcgt gccgtc                                                    256

<210> SEQ ID NO 13
<211> LENGTH: 254
<212> TYPE: DNA
<213> ORGANISM: lettuce
<220> FEATURE:
<221> NAME/KEY: misc_feature
<222> LOCATION: (117)..(117)
<223> OTHER INFORMATION: n is a, c, g, or t

<400> SEQUENCE: 13
tcgacacaaa atccgaggct gtcaggcccc ccacgacgtg gtgaagaagc cacgacgtgg      60
tattgtgatt gatgggtgcc aggtgcgtca cgaaacgtct cgtcaacaga agaggantag    120
aatccctcac cacgacgtgg tgacatggcg cccaaattag ggctataaat agcagccgaa    180
ggtgttgggt tccattgctt atttcttctc tctctctctc tctctctctc tctctctctc    240
tctctcgtgc cgtc                                                      254

<210> SEQ ID NO 14
<211> LENGTH: 17
<212> TYPE: DNA
<213> ORGANISM: Artificial
<220> FEATURE:
<223> OTHER INFORMATION: adapter

<400> SEQUENCE: 14
ctcgtagact gcgtacc                                                    17

<210> SEQ ID NO 15
<211> LENGTH: 15
<212> TYPE: DNA
```

```
<213> ORGANISM: Artificial
<220> FEATURE:
<223> OTHER INFORMATION: adapter

<400> SEQUENCE: 15
aattggtacg cagtc                                                    15

<210> SEQ ID NO 16
<211> LENGTH: 19
<212> TYPE: DNA
<213> ORGANISM: Artificial
<220> FEATURE:
<223> OTHER INFORMATION: primer

<400> SEQUENCE: 16
gtagactgcg taccaattc                                                19

<210> SEQ ID NO 17
<211> LENGTH: 17
<212> TYPE: DNA
<213> ORGANISM: Artificial
<220> FEATURE:
<223> OTHER INFORMATION: primer

<400> SEQUENCE: 17
gactgcgtac caattca                                                  17

<210> SEQ ID NO 18
<211> LENGTH: 17
<212> TYPE: DNA
<213> ORGANISM: Artificial
<220> FEATURE:
<223> OTHER INFORMATION: primer

<400> SEQUENCE: 18
gactgcgtac caattcc                                                  17

<210> SEQ ID NO 19
<211> LENGTH: 16
<212> TYPE: DNA
<213> ORGANISM: Artificial
<220> FEATURE:
<223> OTHER INFORMATION: primer

<400> SEQUENCE: 19
gatgagtcct gagtaa                                                   16

<210> SEQ ID NO 20
<211> LENGTH: 16
<212> TYPE: DNA
<213> ORGANISM: Artificial
<220> FEATURE:
<223> OTHER INFORMATION: primer

<400> SEQUENCE: 20
ctcgatttac acacac                                                   16

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21
agcggataac aatttcacac aggatagact gcgtaccaat                         40
```

<210> SEQ ID NO 22
<211> LENGTH: 373
<212> TYPE: DNA
<213> ORGANISM: pickle

<400> SEQUENCE: 22

| | | | | | |
|---|---|---|---|---|---|
| gaattccggg | gcgaraacca | gaagaaatag | agaggtattg | gataatgact | cacccttgaag | 60 |
| ggtttggaaa | aagaagaaga | ggatgagaga | gacagagaga | tacaggcaat | gagggttcag | 120 |
| kcaataagtc | ctcaaagact | tctgatgggt | tctctacttc | atcgtttgtg | gtctccctga | 180 |
| agataacaat | ctccctaata | gctttagtgt | attacaagta | ccctttctaa | gaacacatgg | 240 |
| tatggaacag | agctatcttt | tatcaatcaa | ataacacagt | ataatttatg | attccaaatc | 300 |
| aaaaactaaa | gcaaagagca | aagactattc | agttcttttg | tgtgtgtgtg | tgtgtgtgtg | 360 |
| tgtgtaaatc | gag | | | | | 373 |

<210> SEQ ID NO 23
<211> LENGTH: 357
<212> TYPE: DNA
<213> ORGANISM: pickle

<400> SEQUENCE: 23

| | | | | | |
|---|---|---|---|---|---|
| gaattccggg | gcgataacca | gaagaaatag | agaggtattg | gataatgact | cacccttgaag | 60 |
| ggtttggaaa | aagaagaaga | ggatgagaga | gacagagaga | tacaggcaat | gagggttcag | 120 |
| kcaataagtc | ctcaaagact | tctgatgggt | tctctacttc | atcgtttgtg | gtctcccaat | 180 |
| ctccctaata | gctttagtgt | attacaagta | ccctttctaa | gaacacatgg | tatggaacag | 240 |
| agctatcttt | tatcaatcaa | ataacacagt | ataatttatg | attccaaatc | aaaaactaaa | 300 |
| gcaaagagca | aagactattc | agttcttgtg | tgtgtgtgtg | tgtgtgtgta | aatcgag | 357 |

<210> SEQ ID NO 24
<211> LENGTH: 21
<212> TYPE: DNA
<213> ORGANISM: Artificial
<220> FEATURE:
<223> OTHER INFORMATION: adapter

<400> SEQUENCE: 24
ctcgtagact gcgtacatgc a         21

<210> SEQ ID NO 25
<211> LENGTH: 14
<212> TYPE: DNA
<213> ORGANISM: Artificial
<220> FEATURE:
<223> OTHER INFORMATION: adapter

<400> SEQUENCE: 25
tgtacgcagt ctac         14

<210> SEQ ID NO 26
<211> LENGTH: 19
<212> TYPE: DNA
<213> ORGANISM: Artificial
<220> FEATURE:
<223> OTHER INFORMATION: primer

<400> SEQUENCE: 26
gtagactgcg tacatgcag         19

```
<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
gactgcgtac atgcagcc                                                    18

<210> SEQ ID NO 28
<211> LENGTH: 16
<212> TYPE: DNA
<213> ORGANISM: Artificial
<220> FEATURE:
<223> OTHER INFORMATION: primer

<400> SEQUENCE: 28
gataagcgga gagaga                                                      16

<210> SEQ ID NO 29
<211> LENGTH: 39
<212> TYPE: DNA
<213> ORGANISM: Artificial
<220> FEATURE:
<223> OTHER INFORMATION: primer

<400> SEQUENCE: 29
agcgataaca atttcacaca ggatagactg cgtacctgc                             39

<210> SEQ ID NO 30
<211> LENGTH: 170
<212> TYPE: DNA
<213> ORGANISM: maize

<400> SEQUENCE: 30
ctgcagccct gccgaccagt ctccgttccc cttcttgtat ttcatggtga gtaataagat      60
tctctctctc tctctcttgt tttttctgtc gaaaaatggg aatcgctaca agtagcatcc     120
gtattttcca ttttttcccg atacgattct ctcttctctc tccgcttatc               170

<210> SEQ ID NO 31
<211> LENGTH: 168
<212> TYPE: DNA
<213> ORGANISM: maize

<400> SEQUENCE: 31
ctgcagccct accgaccagt ctccgttccc cttcttgtat ttcatggtga gaaataagat      60
tctctctctc tcttttggtt tttttctatc gaaaaatggg aattgctaca agtagcatcc     120
gtattttcca ttttttcccg atacgattct cttctctctc cgcttatc                 168

<210> SEQ ID NO 32
<211> LENGTH: 18
<212> TYPE: DNA
<213> ORGANISM: Artificial
<220> FEATURE:
<223> OTHER INFORMATION: primer

<400> SEQUENCE: 32
gactgcgtac caattcca                                                   18

<210> SEQ ID NO 33
<211> LENGTH: 16
```

```
<212> TYPE: DNA
<213> ORGANISM: Artificial
<220> FEATURE:
<223> OTHER INFORMATION: primer

<400> SEQUENCE: 33
gataagcgca cacaca                                                    16

<210> SEQ ID NO 34
<211> LENGTH: 98
<212> TYPE: DNA
<213> ORGANISM: pepper
<220> FEATURE:
<221> NAME/KEY: misc_feature
<222> LOCATION: (25)..(25)
<223> OTHER INFORMATION: n is a, c, g, or t

<400> SEQUENCE: 34
gaattccata aggagagctc gaatnaatga tccattttag ttgaaagttg aaatacagtg    60
catcctctaa taggagtgtg tgtgtgtgtg cgcttatc                            98

<210> SEQ ID NO 35
<211> LENGTH: 95
<212> TYPE: DNA
<213> ORGANISM: pepper
<220> FEATURE:
<221> NAME/KEY: misc_feature
<222> LOCATION: (25)..(25)
<223> OTHER INFORMATION: n is a, c, g, or t

<400> SEQUENCE: 35
gaattccata aggagagctc gaatnaatga tccattttag ttgaaaattg aaatacagtg    60
catcctctaa taggggtgt gtgtgtgcgc ttatc                                95

<210> SEQ ID NO 36
<211> LENGTH: 18
<212> TYPE: DNA
<213> ORGANISM: Artificial
<220> FEATURE:
<223> OTHER INFORMATION: primer

<400> SEQUENCE: 36
gactgcgtac atgcagcg                                                  18

<210> SEQ ID NO 37
<211> LENGTH: 16
<212> TYPE: DNA
<213> ORGANISM: Artificial
<220> FEATURE:
<223> OTHER INFORMATION: primer

<400> SEQUENCE: 37
cagctaagct ctctct                                                    16

<210> SEQ ID NO 38
<211> LENGTH: 16
<212> TYPE: DNA
<213> ORGANISM: Artificial
<220> FEATURE:
<223> OTHER INFORMATION: primer

<400> SEQUENCE: 38
cagcatgact ctctct                                                    16

<210> SEQ ID NO 39
```

```
<211> LENGTH: 16
<212> TYPE: DNA
<213> ORGANISM: Artificial
<220> FEATURE:
<223> OTHER INFORMATION: primer

<400> SEQUENCE: 39
gataagcgct ctctct                                                    16

<210> SEQ ID NO 40
<211> LENGTH: 18
<212> TYPE: DNA
<213> ORGANISM: Artificial
<220> FEATURE:
<223> OTHER INFORMATION: adapter

<400> SEQUENCE: 40
ttaaccatgc gtcagatg                                                  18

<210> SEQ ID NO 41
<211> LENGTH: 17
<212> TYPE: DNA
<213> ORGANISM: Artificial
<220> FEATURE:
<223> OTHER INFORMATION: primer

<400> SEQUENCE: 41
gatgagtcct gagtaat                                                   17

<210> SEQ ID NO 42
<211> LENGTH: 18
<212> TYPE: DNA
<213> ORGANISM: Artificial
<220> FEATURE:
<223> OTHER INFORMATION: primer

<400> SEQUENCE: 42
gactgcgtac caattctg                                                  18

<210> SEQ ID NO 43
<211> LENGTH: 18
<212> TYPE: DNA
<213> ORGANISM: Artificial
<220> FEATURE:
<223> OTHER INFORMATION: primer

<400> SEQUENCE: 43
gactgcgtac caattcgt                                                  18

<210> SEQ ID NO 44
<211> LENGTH: 16
<212> TYPE: DNA
<213> ORGANISM: Artificial
<220> FEATURE:
<223> OTHER INFORMATION: RAMP primer

<400> SEQUENCE: 44
gatagcacga gagaga                                                    16

<210> SEQ ID NO 45
<211> LENGTH: 18
<212> TYPE: DNA
<213> ORGANISM: Artificial
<220> FEATURE:
<223> OTHER INFORMATION: primer

<400> SEQUENCE: 45
```

```
gactgcgtac caattccc                                                18
```

<210> SEQ ID NO 46
<211> LENGTH: 16
<212> TYPE: DNA
<213> ORGANISM: Artificial
<220> FEATURE:
<223> OTHER INFORMATION: RAMP primer

<400> SEQUENCE: 46

```
gactgtacca cacaca                                                  16
```

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47

```
tagtatctga agctcggagg                                              20
```

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48

```
cggacgaagt tccctagcac                                              20
```

<210> SEQ ID NO 49
<211> LENGTH: 21
<212> TYPE: DNA
<213> ORGANISM: Artificial
<220> FEATURE:
<223> OTHER INFORMATION: primer

<400> SEQUENCE: 49

```
caacttgagt tacatttgtg c                                            21
```

<210> SEQ ID NO 50
<211> LENGTH: 50
<212> TYPE: DNA
<213> ORGANISM: Artificial
<220> FEATURE:
<223> OTHER INFORMATION: primer

<400> SEQUENCE: 50

```
cgggagggtt ttcccagtca cgacacgact cactgatgag tcctgagtaa             50
```

<210> SEQ ID NO 51
<211> LENGTH: 21
<212> TYPE: DNA
<213> ORGANISM: Artificial
<220> FEATURE:
<223> OTHER INFORMATION: primer

<400> SEQUENCE: 51

```
gttggatcca ctcttctgat c                                            21
```

<210> SEQ ID NO 52
<211> LENGTH: 20
<212> TYPE: DNA

```
<213> ORGANISM: Artificial
<220> FEATURE:
<223> OTHER INFORMATION: primer

<400> SEQUENCE: 52
gcgttgagca ggcattcgga                                                      20

<210> SEQ ID NO 53
<211> LENGTH: 18
<212> TYPE: DNA
<213> ORGANISM: Artificial
<220> FEATURE:
<223> OTHER INFORMATION: primer

<400> SEQUENCE: 53
gatgagtcct gagtaatc                                                        18
```